(12) United States Patent
West, Jr. et al.

(10) Patent No.: US 7,118,578 B2
(45) Date of Patent: *Oct. 10, 2006

(54) APPARATUS AND METHODS FOR INDEPENDENTLY CONDITIONING AND PRE-TENSIONING A PLURALITY OF LIGAMENT GRAFTS DURING JOINT REPAIR SURGERY

(75) Inventors: Hugh S. West, Jr., Salt Lake City, UT (US); John R. West, Cincinnati, OH (US)

(73) Assignee: HS West Investments, LLC, Salt Lake City, UT (US)

( * ) Notice: Subject to any disclaimer, the term of this patent is extended or adjusted under 35 U.S.C. 154(b) by 309 days.

This patent is subject to a terminal disclaimer.

(21) Appl. No.: 10/651,671

(22) Filed: Aug. 29, 2003

(65) Prior Publication Data

US 2004/0039389 A1 Feb. 26, 2004

Related U.S. Application Data

(63) Continuation-in-part of application No. 09/711,488, filed on Nov. 13, 2000, now Pat. No. 6,679,889.

(51) Int. Cl.
*A61B 17/58* (2006.01)
*A61B 17/60* (2006.01)
*A61F 2/00* (2006.01)
*A61F 2/32* (2006.01)
*A61F 2/34* (2006.01)

(52) U.S. Cl. ..................................... 606/88
(58) Field of Classification Search .............. 606/73, 606/88, 96, 102, 103, 233
See application file for complete search history.

(56) References Cited

U.S. PATENT DOCUMENTS

| 3,842,824 A | * | 10/1974 | Neufeld ................... 606/73 |
| 4,301,551 A | | 11/1981 | Dore et al. |
| 4,400,833 A | | 8/1983 | Kurland |
| 4,467,478 A | | 8/1984 | Jurgutis |
| 4,590,928 A | | 5/1986 | Hunt et al. |
| 4,597,766 A | | 7/1986 | Hilal et al. |

(Continued)

OTHER PUBLICATIONS

"Intrafix™ Technique for Tibial Fixation of ACL Grafts," Joseph H. Sklar, M.D., Innovasive Devices, 1999.

*Primary Examiner*—Eduardo C. Robert
*Assistant Examiner*—John Kim
(74) *Attorney, Agent, or Firm*—Workman Nydegger

(57) ABSTRACT

Apparatus and methods for conditioning and pre-tensioning soft tissue grafts during joint repair surgery, such as during repair of the anterior cruciate ligament (ACL). The inventive apparatus is advantageously adapted and configured so as to enable a surgeon to independently apply a desired tensile load to individual graft strands or graft bundles of a multi-strand tissue graft. The inventive methods enable each graft strand or bundle to be properly tensioned so as to both "condition" the graft to prevent subsequent stretching, relaxation or elongation following surgery, which can destabilize the joint, and to pre-tension each graft strand or bundle to a predetermined amount so that each contributes to the strength and stability of the joint, thus resulting in a stronger and more durable joint. The tensioning device is advantageously equipped with structure for attachment to a patient's limb during the conditioning and pre-tensioning procedure. It has multiple adjustable tension applicators that can be independently manipulated so as to apply a separate tensile load to one or more ends of a tissue graft strand attached to each adjustable tension applicator.

24 Claims, 29 Drawing Sheets

U.S. PATENT DOCUMENTS

| | | |
|---|---|---|
| 4,605,414 A | 8/1986 | Czajka |
| 4,668,233 A | 5/1987 | Seedhom et al. |
| 4,712,542 A | 12/1987 | Daniel et al. |
| 4,739,751 A | 4/1988 | Sapega et al. |
| 4,744,793 A | 5/1988 | Parr et al. |
| 4,772,286 A | 9/1988 | Goble et al. |
| 4,773,417 A | 9/1988 | Moore et al. |
| 4,834,752 A | 5/1989 | Van Kampen |
| 4,870,957 A | 10/1989 | Goble et al. |
| 4,927,421 A | 5/1990 | Goble et al. |
| 4,950,270 A | 8/1990 | Bowman et al. |
| 4,950,271 A | 8/1990 | Lewis et al. |
| 4,997,433 A | 3/1991 | Goble et al. |
| 5,037,426 A | 8/1991 | Goble et al. |
| 5,108,433 A | 4/1992 | May et al. |
| 5,129,902 A | 7/1992 | Goble et al. |
| 5,139,520 A | 8/1992 | Rosenberg |
| 5,147,362 A | 9/1992 | Goble |
| 5,207,703 A * | 5/1993 | Jain .................. 606/232 |
| RE34,293 E | 6/1993 | Goble et al. |
| 5,507,750 A | 4/1996 | Goble et al. |
| 5,562,668 A | 10/1996 | Johnson |
| 5,630,820 A | 5/1997 | Todd |
| 5,713,897 A | 2/1998 | Goble et al. |
| 5,964,764 A | 10/1999 | West, Jr. et al. |
| 5,980,473 A | 11/1999 | Korakianitis et al. |
| 6,001,106 A | 12/1999 | Ryan et al. |
| 6,036,694 A | 3/2000 | Goble et al. |
| 6,279,415 B1 | 8/2001 | Chance et al. |

\* cited by examiner

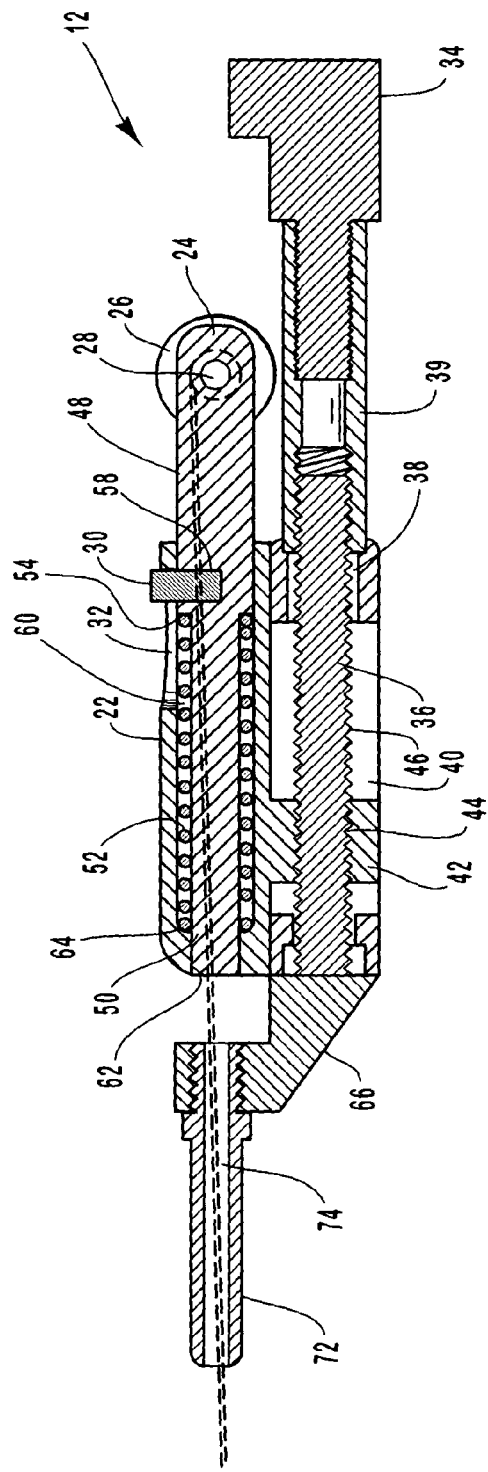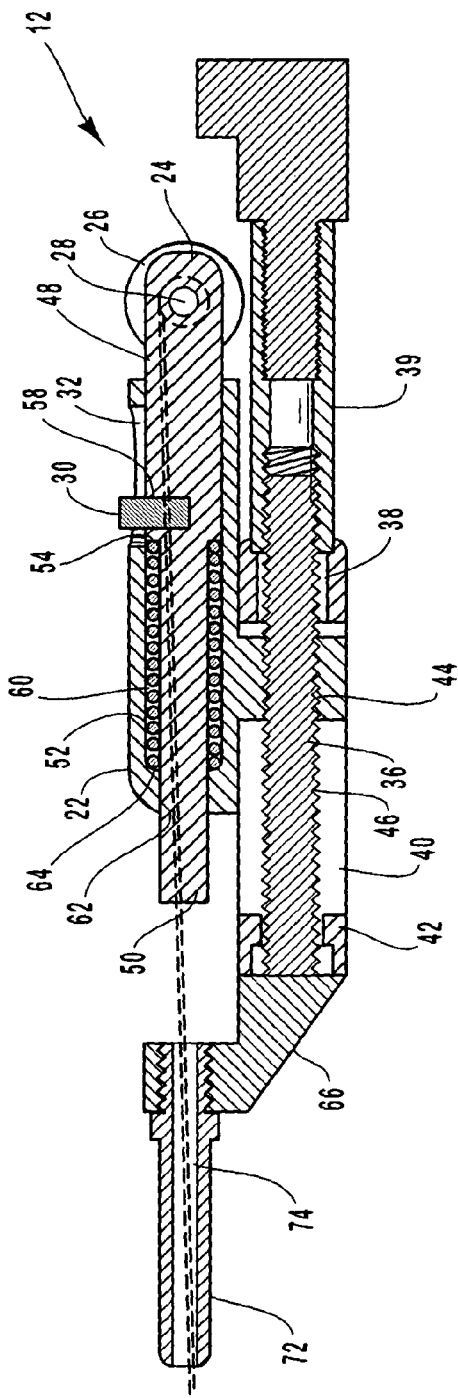

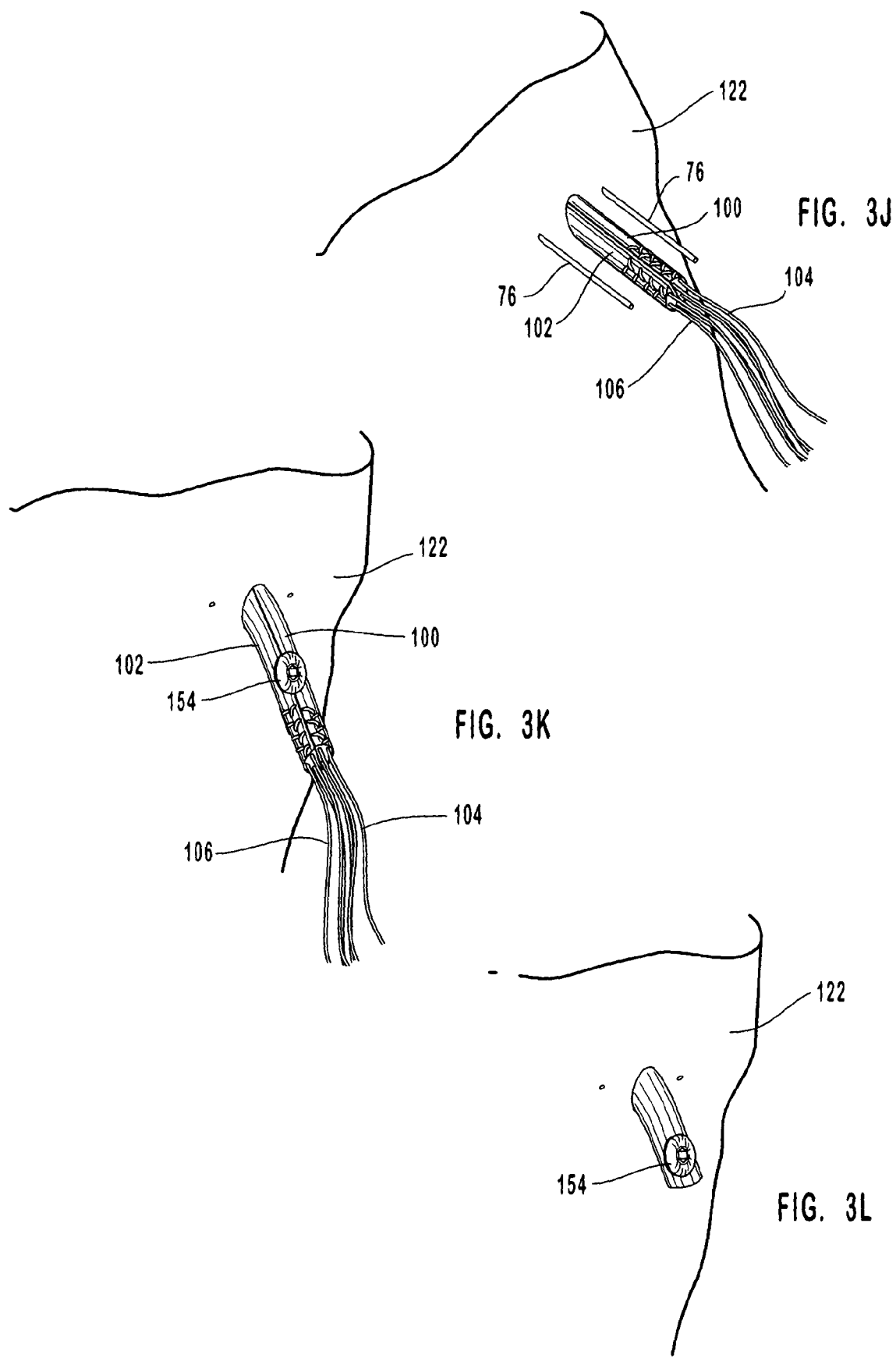

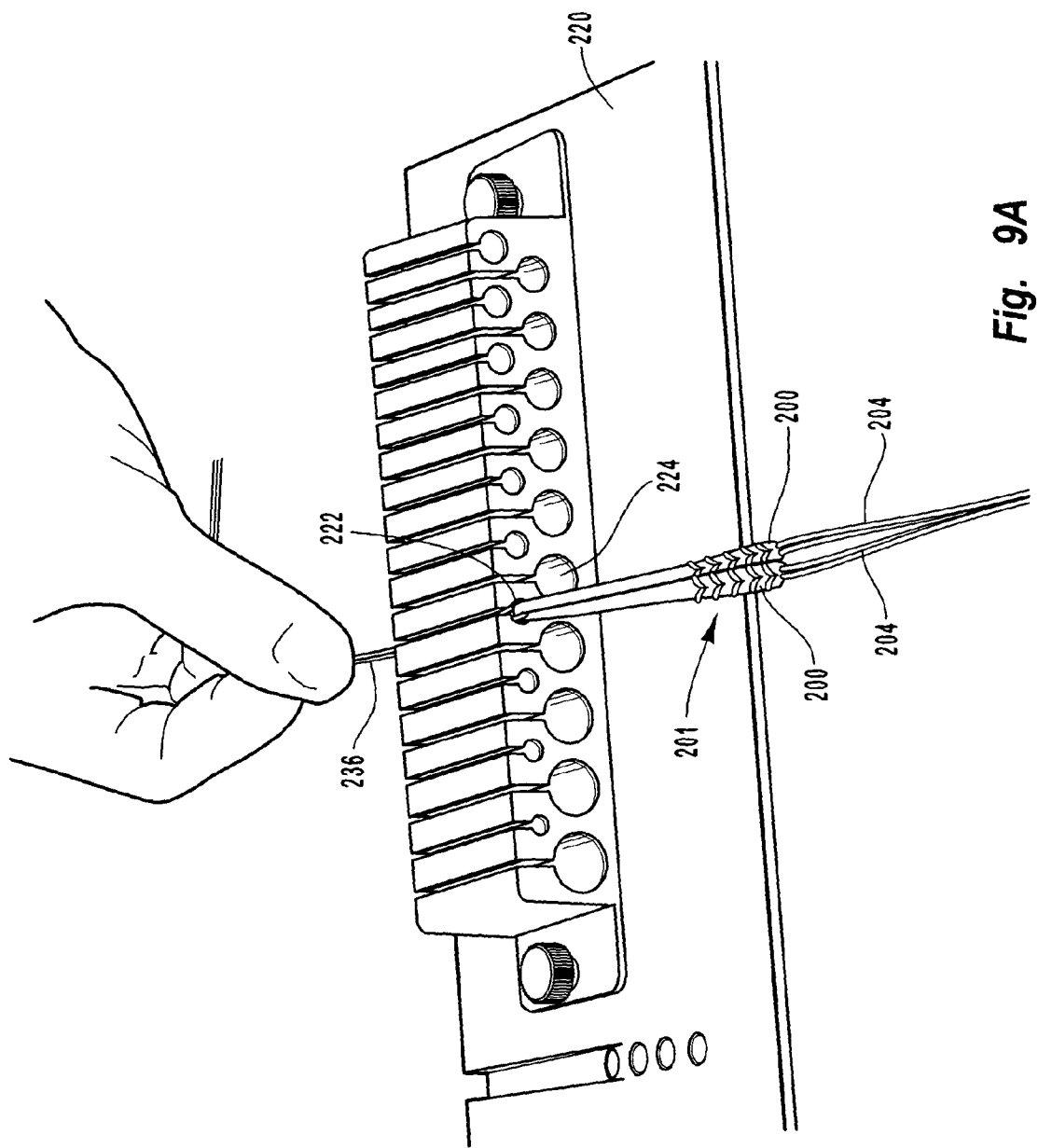

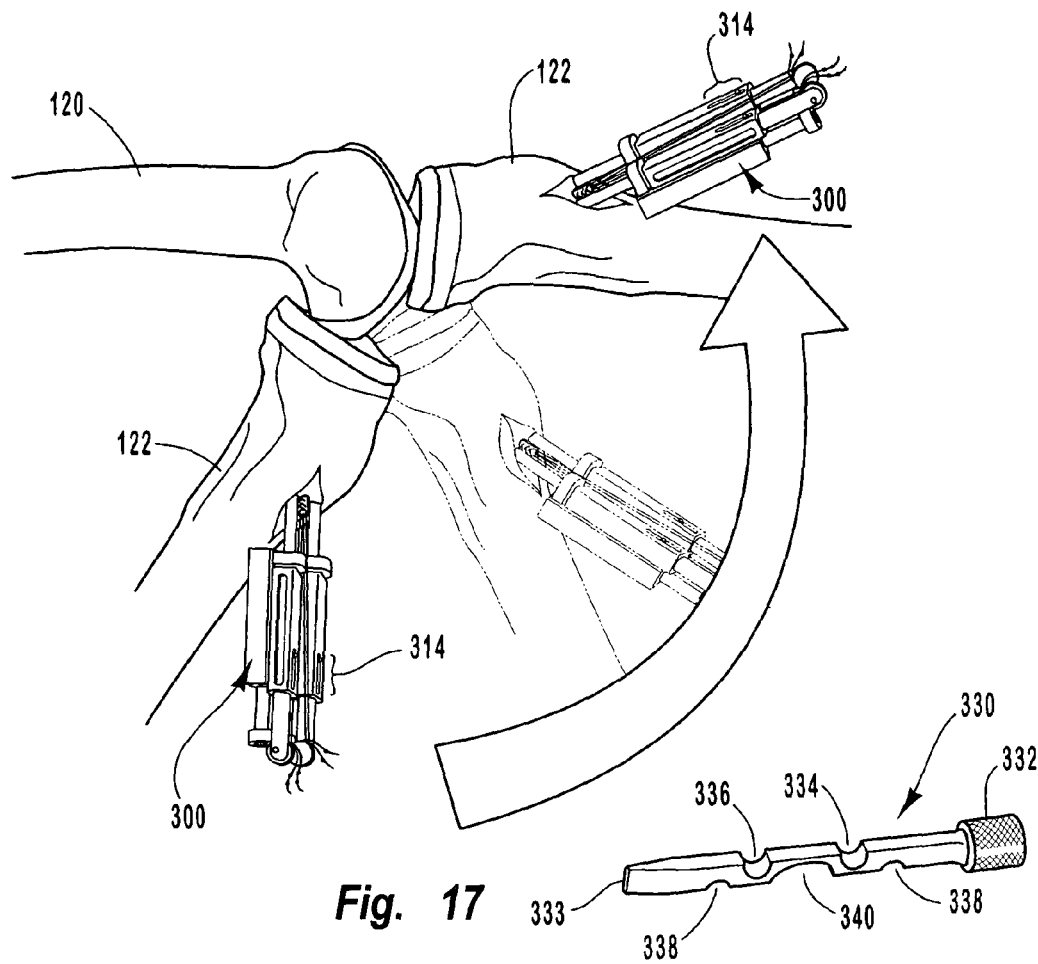
Fig. 17
Fig. 18A
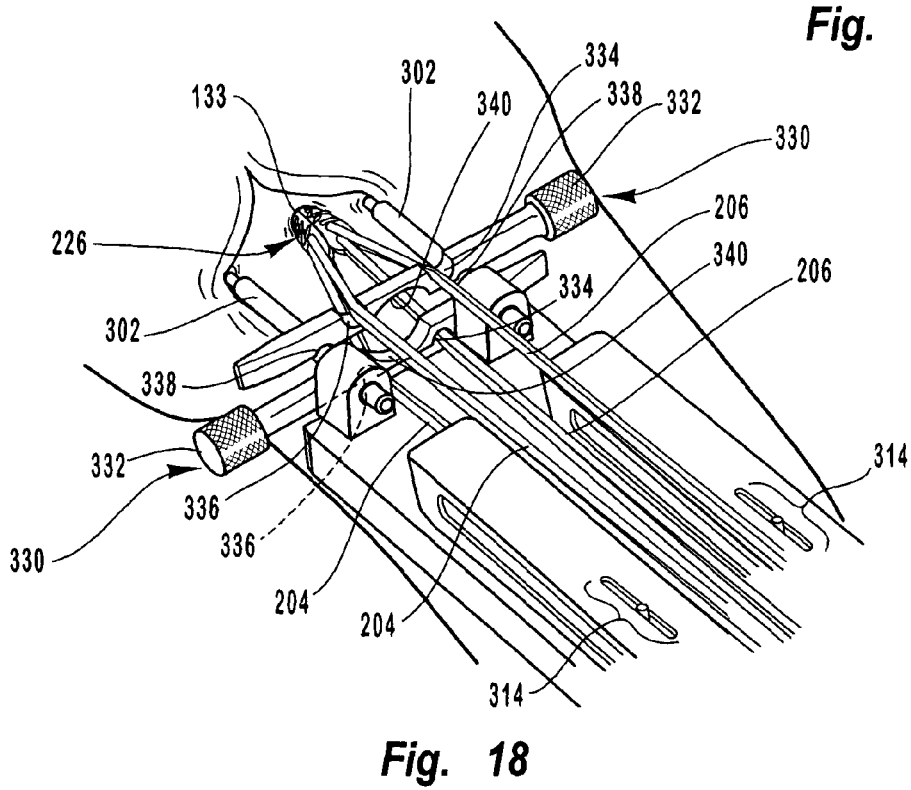
Fig. 18

APPARATUS AND METHODS FOR INDEPENDENTLY CONDITIONING AND PRE-TENSIONING A PLURALITY OF LIGAMENT GRAFTS DURING JOINT REPAIR SURGERY

CROSS-REFERENCE TO RELATED APPLICATIONS

This application is a continuation-in-part of U.S. application Ser. No. 09/711,488, filed Nov. 13, 2000 now U.S. Pat. No. 6,679,889. The disclosure of the foregoing application is incorporated herein in its entirety.

BACKGROUND OF THE INVENTION

1. The Field of the Invention

The present invention is in the field of joint repair surgery, such as reconstruction of the anterior cruciate ligament (ACL). More particularly, the invention relates to tensioning devices for applying loads to soft tissue grafts used in joint repair procedures.

2. The Relevant Technology

Injuries to joints, specifically the knee, are quite common, particularly when one engages in vigorous sporting activities. A common injury is a rupture or tear of the anterior cruciate ligament ("ACL"), which is the primary ligament responsible for holding the knee joint together and which keeps it from slipping out of joint or dislocating. An unrepaired ruptured or torn ACL can cripple, and would most certainly limit physical activity of, the person suffering a ruptured or torn ACL. Absent reconstruction of the ACL, such injuries would likely be the end of professional sports careers and would prevent ordinary people from enjoying an active life involving sports and like recreation.

Improvements in surgical procedures have made ACL reconstruction procedures more successful and more common. In general, an ACL reconstruction procedure involves taking a soft tissue graft from another part of the body, such as the patellar tendon or the hamstrings, and attaching it at both ends through a hole drilled through the two bones that make up the knee joint: the femur and the tibia. When secured in place, the soft tissue graft will mimic and take the place of the ACL itself. This soft tissue graft holds the femur and tibia together to make the joint more stable, but is flexible enough to allow for normal joint movements (i.e., flexion and extension).

Graft tension in ACL reconstruction has been recognized as an important factor in the clinical outcome of the ACL reconstruction procedure. Grafts that are too loose may be unstable, and grafts that are too tight may greatly restrict motion of the knee. Recent interest in graft tension and scientific work on the subject have raised the demand for quality instruments that will assist the surgeon in more effectively fixing ligament grafts under known tension.

Publications in the past few years have emphasized the need for adequate tensioning of the graft. These include Markolf et al., "Biomechanical Consequences of Replacement of the Anterior Cruciate Ligament With a Patellar Ligament Allograft. Part Two: Forces in the Graft Compared with Forces in the Intact Ligament," *J. Bone Joint Surg. Am.*, 78:11, 1728–34 (November 1996); Tohyama et al., "Significance of Graft Tension in Anterior Cruciate Ligament Reconstruction. Basic background and clinical outcome," *Knee Surg. Sports Traumatol. Arthroscopy*, 6 Suppl. 1, S30-7 (1998); Andersen et al., "Review on Tension in the Natural and Reconstructed Anterior Cruciate Ligament," *Knee Surg. Sports Traumatol. Arthroscopy*, 2:4, 192–202 (1994); Yasuda et al., "Effects of Initial Graft Tension on Clinical Outcome After Anterior Cruciate Ligament Reconstruction. Autogenous Doubled Hamstring Tendons Connected in Series of Polyester Tapes," *Am. J. Sports Med.*, 25:1, 99–106 (January 1997). For purpose of disclosure, the foregoing publications are incorporated herein by specific reference.

While much of the focus has been directed to the issue of under tensioning, which typically results in knees that are less stable than normal, application of too much tension may in theory also have an adverse effect by constraining the joints or causing increased pressure on articular surfaces.

A recent study by Hamner et al. has added to the understanding of graft tension by demonstrating that unequal tension in the individual strands of the soft tissue graft can result in significant losses in total graft strength and stiffness. Hamner et al., "Hamstring Tendon Grafts for Reconstruction of the Anterior Cruciate Ligament: Biomechanical Evaluation of the Use of Multiple Strands and Tensioning Techniques," *J. Bone Joint Surg. Am.*, 81:4, 549–57 (April 1999). Hamner et al. studied whether tensioning the soft tissue strands by hand would result in equalization of the load borne by each strand. Hamner et al. showed that this method was not effective in equalizing the load on the strands, which led to an ultimate graft strength that was not significantly greater than the strength of the individual strands taken alone.

Previous work has been done to develop and patent devices that are used to apply a known tension to cruciate ligament grafts. Such devices have typically included simple spring scales that apply a known load to the graft as a whole. E.g., U.S. Pat. No. 4,712,542; U.S. Pat. No. 5,037,426; U.S. Pat. No. Re 34,762; U.S. Pat. No. 5,713,897; U.S. Pat. No. 5,507,750; and U.S. Pat. No. 5,562,668. For purposes of disclosing mechanisms for applying a known load or tension onto a soft tissue graft, the foregoing patents are incorporated herein by specific reference.

Because none of the foregoing references disclose any method for using these devices to separately tension multiple soft tissue grafts so as to equalize the stress applied to each, one strand will often be preferentially loaded more than another, thus resulting in disparately conditioned and pre-tensioned strands that are not significantly stronger or stiffer than a single strand. More particularly, because hamstrings can have different diameters, simply applying a standard load to both strands simultaneously could result in one graft being subjected to a different material stress than the other graft. Moreover, even in the case of hamstrings or other soft tissue grafts that have the same or substantially the same diameters, inadvertent or unavoidable error by the treating surgeon, such as unequal conditioning of each soft tissue graft, can still lead to uneven loads being borne by each individual graft. Regardless of the causes for unequal application of material stress to each of the individual soft tissue grafts, the "tighter" graft (or graft with higher material stress) will reach the failure point first, thereby causing a lower load to failure for the composite graft.

In view of the foregoing, it would be an improvement in the art of joint repair to provide apparatus and methods for independently conditioning and pre-tensioning individual soft tissue graft strands, such as a pair of hamstrings used in an ACL reconstruction procedure.

It would be an additional improvement in the art to provide apparatus and methods for conditioning and pre-tensioning individual graft strands so that each graft strand could substantially contribute to the overall strength and stability of the repaired joint.

SUMMARY OF THE INVENTION

The present invention encompasses apparatus and methods for independently tensioning a plurality of soft tissue grafts during joint repair procedures, such as in procedures to replace or augment the anterior cruciate ligament ("ACL"). Because of the desirability of implanting soft tissue grafts having a predetermined tension, but because of the tendency of soft tissue grafts to relax or stretch after being implanted, it is often desirable to "condition" such grafts prior to anchoring them in place. Soft tissue grafts can be "conditioned" by applying a tensile load for a sufficient amount of time order to prevent further stretching or relaxation of the tissue graft and/or attached sutures over time after being implanted. In addition to conditioning, it is also generally desirable to pre-stress (or pre-tension) the soft tissue grafts in order to ensure a desired degree of joint stability and strength. Thus, both conditioning and pre-tensioning are procedures which can ensure the success of the joint repair surgery.

Grafts are advantageously "conditioned" prior to being pre-tensioned in order to take the play out of the system. Conditioning assists in tightly seating the graft within the bone tunnel and also assists in fully seating or tightening the sutures tied to the tissue graft. After the play has been taken out of the system the individual grafts can be more reliably pre-stressed to a desired degree. Attempting to apply a desired amount of material stress to a graft that has not been adequately conditioned may result in the decay or diminution of actual material stress born by the graft over time. This can lead to long-term instability of the joint.

A predetermined amount of material stress is advantageously applied to the soft tissue grafts in order to yield a joint having a desired amount of stability and stiffness. Inadequately tensioned soft tissue grafts can yield a joint that is not adequately stable or which is too loose, thus being far more prone to subsequent injury and possible rupture of the tissue grafts. Grafts that have been over tensioned can yield joints that are too stiff and that lack adequate flexibility.

Unless the soft tissue strands of a multiple strand graft are properly pre-tensioned based on their relative size and strength, the strand that initially bears a disproportionately high amount of material stress will reach the failure point and rupture first when the graft is subjected to high stress. Subsequently, the graft initially bearing a disproportionately low amount of material stress will then bear all the stress and be more prone to failure since it will be acting on its own to hold the joint together. In short, a soft tissue graft that includes multiple strands that are not properly conditioned and/or pre-tensioned may result in a joint that is more elastic and/or that has a significantly lower composite load-to-failure point.

Notwithstanding the importance of ensuring that each strand of a multiple stranded tissue graft is properly pre-tensioned so that each strand properly contributes an appropriate level of strength to the composite graft based on their relative size and stiffness, it has heretofore been difficult to condition and pre-tension each strand to an appropriate level. As a result, it has heretofore been difficult to ensure that each strand contributes appropriately to the strength and stability of the joint.

The present invention proposes novel apparatus and methods that enable a practitioner to independently condition and pre-tension multiple strands of a multi-strand soft tissue graft. The tensioning devices according to the present invention may be used to apply a desired amount of tension or load to single- or multi-stranded grafts. In a preferred embodiment, the inventive apparatus comprises a tensioning device that includes a plurality of separately adjustable tension applicators (e.g., two) capable of independently applying a desired level of tension to each of the plurality (e.g., two) of soft tissue grafts used in the joint repair surgery. The tensioning device may further include attachment means for removably attaching the device to a patient's bone or limb during the surgical procedure.

An advantage of the inventive tensioning device is the ability to condition and pre-tension the graft after implantation at one end but before final fixation. In the case of an ACL reconstruction procedure, the graft may advantageously be conditioned prior to pre-tensioning by repeatedly flexing and extending the patient's knee under load to remove any laxity or looseness in the graft construct.

The proposed device is advantageously free-standing on the tibia, which can free the surgeon's hands to set knee flexation angle and fix the distal end of the graft while monitoring tension. The device may also be able to sustain a load on the graft for static loading so as to help stretch the graft before fixation.

In one embodiment, each adjustable tension applicator of the tensioning device includes attachment means for securing one or more sutures attached to a strand of the soft tissue graft and an adjustable biasing mechanism (e.g., a spring-loaded mechanism) capable of applying a measured tensile load to the sutures and associated soft tissue graft strand. In one embodiment, the adjustable biasing mechanism further includes an immobile base or block, a cylinder block or module slidably disposed on the immobile base, a tensioning piston slidably disposed within a portion of the cylinder block, a biasing spring communicating between the cylinder block and the tensioning piston, and a rotatable adjustment knob threadably attached to the cylinder block, which, upon turning, selectively urges the cylinder block towards or away from the tensioning piston so as to selectively compress or extend the biasing spring and thereby increase or decrease the load applied by the biasing spring onto the tensioning piston.

The means for securing the one or more sutures to the tensioning pistons may advantageously include a suture attachment wheel rotatably connected to each tensioning piston. Free rotation of the suture attachment wheel ensures equal tension being applied to each side of a looped suture strand. This is particularly useful in the case of a looped tissue graft strand that has two free ends after initial attachment of one end of the graft (i.e., the end of the graft that is doubled over). One or more sutures may be attached to each of the two free ends of the graft strand and then tied together to form a continuous suture loop that can be looped around the suture attachment wheel. Free rotation of the suture loop around the suture attachment wheel equalizes the tension applied to each of the two free ends of the graft strand. A separate suture attachment wheel may be provided for each looped graft strand.

While the tensioning device is in use, outward movement of the tensioning piston relative to the slidable cylinder block as the compressive force applied by the biasing spring is restricted by the countervailing inward tension exerted by the soft tissue graft attached to the tensioning piston by means of the sutures. Thus, during conditioning and subsequent pre-tensioning of the soft tissue graft, the tensioning piston may only move a few millimeters, or less, as the soft tissue graft is conditioned and/or tensioned. Turning of the adjustment knob causes the cylinder block to move either towards or away from the tensioning piston. Movement of the cylinder block towards the tensioning piston causes the biasing spring to become progressively compressed, thus increasing the outward, or compressive, force exerted by the spring onto the piston. This, in turn, increases the tension applied to the tissue graft strand. Likewise, movement of the cylinder block away from the piston progressively decompresses the biasing spring, thus decreasing the compressive force exerted by the spring onto the piston. This, in turn, decreases the tension applied to the tissue graft strand.

The magnitude of compressive force exerted by the biasing spring onto the piston is essentially equivalent to the magnitude of the tensile force exerted onto the soft tissue graft by the tensioning piston. Because the amount of compressive force exerted by a spring is directly related to the distance that the spring has been compressed relative to its relaxed position, the compressive load exerted by the spring onto the tensioning piston, and the tensile load exerted by the tensioning piston onto the soft tissue graft, can be indirectly measured by measuring the distance the spring has been compressed. Thus, the adjustable biasing mechanism may advantageously be equipped with a gauge or other means for measuring the magnitude of spring compression so as to indirectly measure the amount of tensile load being exerted on the soft tissue graft during conditioning and pre-tensioning.

Notwithstanding the foregoing, one will readily appreciate, in view of the disclosure herein, that inventive devices according to the invention are not limited to any particular mechanism for performing the task of independently tensioning a plurality of strands of a soft tissue graft. The mechanisms described herein are merely illustrative and exemplary. For example, the tension loading or measuring function could alternatively be provided by a variety of simple scales, such as tension springs, compression springs, torsion springs or electronic transducers. In addition a variety of electronically actuated load measuring and tensioning devices are certainly within the scope of the invention so long as they are capable of independently tensioning separate soft tissue grafts. Examples include a strain gauge, a rotary gauge, an LVDT and the like.

The tensioning device can potentially be used to monitor isometry and measure tension in a single strand of a soft tissue graft. The current design could also be altered in order to incorporate additional adjustable tension applicators that can exert and measure tension in as many tissue graft stands as a surgeon might choose to include in the soft tissue graft.

In a preferred method for carrying out procedures according to the invention, a plurality of soft tissue grafts (e.g., two) are taken from the patient, such as from the ham strings or patellar tendon, drawn through holes bored through the femur and tibia according to known surgical procedures, and attached to the femur according to known surgical procedures. In one embodiment, the tissue strands are doubled over to form a looped strand having a doubled over end that is attached to the femur and two free ends that will ultimately be attached to the tibia. Sutures are attached to the free end(s) of the soft tissue graft at an appropriate point during the implantation procedure using known methods. In one embodiment, the sutures and a portion of the tissue graft extend out of an access hole in the patient's leg near the hole in the tibia.

Thereafter a tensioning device capable of independently applying a tensile load to each strand of the soft tissue graft is provided, an example of which is the preferred device described more fully herein. The tensioning device will advantageously include two or more adjustable tension applicators corresponding to two or more soft tissue graft strands, respectively. The tensioning device is then attached to the patient's bone or limb by means of guide pins drilled into the bone, or some other appropriate manner (i.e., by means of a belt or band wrapped around the patient's leg), followed by attaching the suture or suture loop associated with one of the strands of the tissue graft to one adjustable tension applicator and attaching the suture or suture loop associated with another one of the strands of the tissue graft to another adjustable tension applicator. In the case of a modular tensioning device, the module responsible for securing the tensioning device to the patient's tibia is advantageously attached to the leg first. Thereafter, the module responsible for applying the tensile load to the soft tissue grafts is attached to the attachment module. Of course, a single, non-modular unit may also be employed.

After the sutures have been secured to the tensioning device, the tensioning device is used to independently apply a desired tensile load to each strand of a multi-stranded soft tissue graft. This may be done, for example, by tightening the tension knobs of each adjustable tension applicator described above so as to compress the biasing spring and thereby apply a corresponding compressing force onto each tensioning piston, which is essentially equal to the magnitude of the tensile load exerted by the tensioning piston onto the soft tissue graft strand.

Thereafter, the joint (e.g., the knee) is advantageously "cycled" by the treating physician, i.e., by alternatively flexing and extending the joint over an angular distance between 0° and 90° a number of times (e.g., 25 repetitions) in order to assist in conditioning the soft tissue graft strands and also to test the joint stability. A process of altering the tensile load applied to each of the soft tissue graft strands by the tensioning device followed by cycling of the joint can repeated until a desired level of conditioning, pre-stressing and associated joint stability and strength are achieved. When negligible losses in joint stability are observed, the free ends of the soft tissue graft are secured to the bone (e.g., the tibia) by appropriate anchoring means known in the art, or by means of the novel implantable anchor device disclosed herein.

An example of anchoring means known in the art is an interference screw, which is screwed directly into the hole in the patient's bone (e.g., the tibia) through which the soft tissue graft is passed by means of a driver. After the interference screw has been screwed in place, the driver and tensioning device are removed. If guide pins are used to secure the tensioning device to the person's leg, these are also removed. The remaining portion of the soft tissue graft that extends beyond the bone may be secured to the outer surface of the bone by securing means known in the art, e.g., a spiked washer, staple or post in order to reinforce fixation of the graft. Alternatively, it may simply be removed. The graft is trimmed to remove the sutures, and the incision in the leg is closed.

In an alternative embodiment, a novel implantable anchor device may be employed to secure the soft tissue graft to the tibia or other bone. An exemplary anchor includes a cylindrical outer sheath having a cylindrical outer wall and a generally cylindrical bore therethrough, and a corresponding locking core or shaft used to lock the sutures into place once the conditioning and pre-tensioning procedure has been completed. The circumference of the outer sheath is selected to fit within the hole bored through the tibia or other bone.

The bottom part of the outer sheath, or the part of the sheath which faces the bone, includes a plurality of suture holes disposed near the outer edge of the sheath adjacent to the cylindrical outer wall. The suture holes permit passage therethrough of the individual strands of the sutures attached to the free ends of the soft tissue graft. The outer sheath, inward of the suture holes, may be closed or include a hole through center of the sheath bottom face. A hole permits the passage therethrough of an interference screw, post, or other device capable of urging the soft tissue graft against the walls of the hole through the bone to promote faster adhesion thereto. The use of an interference screw also strengthens the fixation of the graft to the bone.

The top part of the sheath, or the part of the sheath facing away from the bone, includes a lip or other protrusion extending laterally from the edge of cylindrical outer wall. When the anchor device is placed into the bore within the tibia or other bone, the lip or other protrusion advantageously overlaps the outer surface of the bone, thus acting as a stop to hold the anchor device in a desired location. The inward tension exerted by the soft tissue graft onto the sutures effectively pulls the lip or protrusion against the bone, thus reliably locking the anchor device against the bone.

The locking core is capable of sliding into and out of the outer sheath, but has a slightly tapered outer wall so that it can form an increasingly tighter compression fit with the inner wall of the outer sheath as it is pressed or forced into the sheath. The locking core is preferably hollow and includes suture passages passing through the bottom edge nearest, and corresponding to, the suture holes of the outer sheath. The suture passages pass approximately longitudinally through the locking core but at an angle so that they exit through the outer wall of the locking core rather than the top edge, or the edge facing away from the outer sheath. In this way, the sutures will pass through the locking core in a manner so that, when the locking core is deployed, the sutures will be tightly pinched between the outer wall of the locking core and the inner wall of the outer sheath. This pinching action prevents the sutures from slipping back into the bone hole, thus maintaining the desired tension on the sutures and associated soft tissue graft strands after conditioning and pre-tensioning of the individual graft strands, as described more fully herein. Prior to deployment of the locking core, the sutures are free to slide inwardly or outwardly as desired relative to the outer sheath and the locking core, which allows the tensioning device to increase or decrease the tensile load applied to the soft tissue graft strands, as desired.

These and other advantages and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages aid objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which:

FIG. 2 is a side cross-sectional view of the tensioning device depicted in FIG. 1 taken along line 2—2;

FIG. 2A shows the tensioning device of FIG. 2 after compression of the biasing spring to increase to tensile load exerted by the tensioning piston;

FIGS. 3A–3L illustrate an exemplary procedure for conditioning, pre-tensioning, and mounting of a multiple strand tissue graft within a bone tunnel using a tensioning device according to the invention;

FIGS. 9A and 9B show a perspective view of a tissue graft thickness measuring device;

FIG. 17 depicts the act of cycling the joint in order to condition the soft tissue graft;

FIGS. 18 and 18A depict a pair of suture strand separators used to separate a plurality of suture strands into four quadrants;

DETAILED DESCRIPTION OF THE PREFERRED EMBODIMENTS

Figure 1:
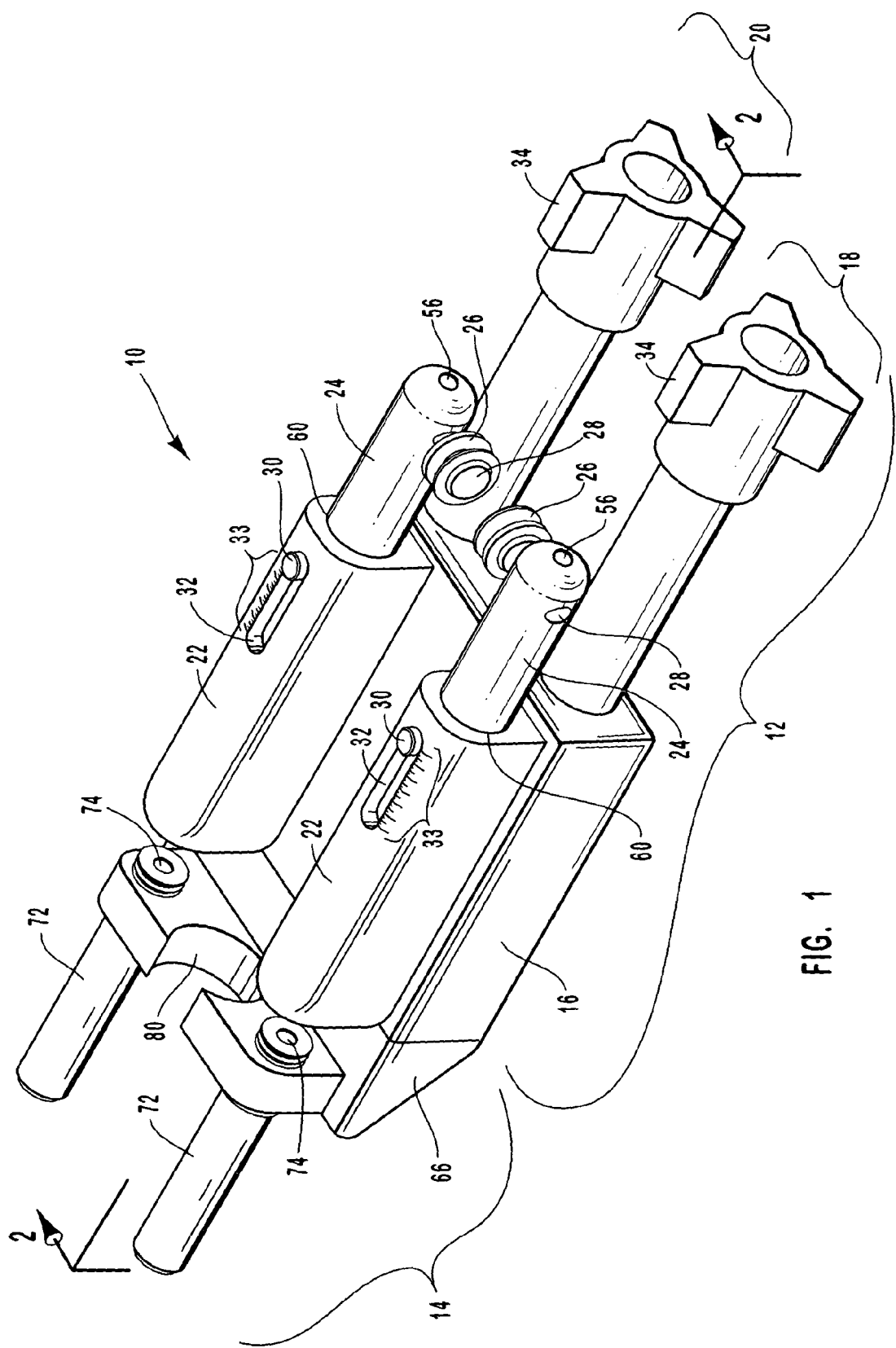
FIG. 1 is a perspective view of a tensioning device according to the invention.

The present invention is directed to apparatus and methods for independently tensioning a plurality of soft tissue grafts (e.g., two) during joint repair procedures, such as in procedures to replace the anterior cruciate ligament (ACL). In order for the soft tissue graft to provide adequate joint stability and provide a predetermined amount of strength, but because of the tendency of many soft tissue grafts (e.g., ham strings) and/or sutures attached thereto to relax after the graft has been implanted, it is often desirable to "condition" the graft prior to being permanently anchored to the bone. Conditioning is advantageously performed to take the play out of the system and to ensure adequate seating of the graft prior to pre-stressing. It may also be desirable to pre-stress (or pre-tension) the soft tissue graft to provide a predetermined amount of joint stability and strength. Thus, conditioning and pre-tensioning of the soft tissue grafts can help to ensure the success of the surgical procedure.

Where multiple strands of soft tissue are used as the ligament graft, it is often difficult or even impossible using existing devices and procedures to ensure that each graft strand bears an appropriate load. Unless each graft strand is properly conditioned and pre-tensioned, it is unlikely that each of the soft tissue strands will bear an appropriate load and properly contribute to the strength of the joint. Evidence has shown that a graft strand that has been inadequately conditioned and pre-tensioned may bear little, if any, of the load applied to the joint during normal use absent stretching or tearing of a more highly conditioned and pre-tensioned strands. In the case of grafts comprising a pair of hamstring strands, one of which is improperly conditioned and pre-tensioned, the majority of the load will be born by the strand that has been more fully conditioned and pre-tensioned.

Existing apparatus and procedures are only able to apply tension to multiple-stranded grafts as a group, rather than individually. Such procedures often result in one strand being better conditioned and pre-tensioned than the other for at least two reasons. First, unavoidable or inadvertent error in how the sutures are initially tied to the soft tissue grafts may result in the failure to apply an equal load to each of the strands. In other words, one of the sets of sutures attached to one of the soft tissue strands may become taught before the other set or sets of sutures attached to the other soft tissue strand(s), thus resulting in proper conditioning and pre-tensioning of only that strand that is first subjected to the tensile load.

Second, not all ham strings or other soft tissue grafts are of equal cross-section and/or stiffness. Thus, some strands may undergo, or allow for, greater stretching (or "strain") before the desired level of tensile load has been applied to the strand to ensure proper "conditioning" and subsequent pre-tensioning. Strands of greater cross-section may also require being subjected to a higher tensile load to become properly conditioned. The sutures tied to each strand of a multiple-stranded graft may not be equally tight initially before condition, thus possibly requiring different magnitudes of "strain" (or pulling distance) on different strands to achieve the same degree of conditioning. An apparatus or procedure that is unable to adjust for such variations in tissue graft stiffness or cross-sectional diameter may be incapable of ensuring proper conditioning and subsequent pre-tensioning of each strand of the soft tissue graft. The same is true for the inability to account for inherent variations in initial suture tautness or other systematic or random variations in how the surgeon ties the individual sutures to each soft tissue graft strand.

The present invention proposes novel apparatus and methods to solve the foregoing problems. More particularly, the inventive apparatus comprises a tensioning device that includes a plurality of separate adjustable tension applicators (e.g., two) capable of independently applying a desired level of tension to each of the plurality (e.g., two) of strands of the soft tissue graft used in the joint repair surgery. The tensioning device may further include attachment means for removably attaching the device to a patient's bone or limb during the surgical procedure. Reference is now made to the Drawings, which illustrate exemplary apparatus and methods according to the invention.

An illustrative tensioning device capable of independently conditioning and applying tension to two separate soft tissue strands, or groups of strands, is depicted in FIG. 1. In particular, FIG. 1 depicts a tensioning device 10 that is modular, i.e., that includes two separate and detachable substructures or systems, namely a tensioning system 12 and a limb attachment system 14. The tensioning system 12 further includes a pair of adjustable tension applicators capable of independently applying tension to each of a pair of soft tissue strands, or groups of strands. As shown in FIG. 1, the tensioning system 12 includes a tensioning block or module 16. Attached to, or associated with, the tensioning module 16 are a first adjustable tension applicator 18 and a second adjustable tension applicator 20, which are essentially mirror images of each other. Because of this, each of the exemplary first and second adjustable tension applicators 18 and 20 depicted in FIG. 1 may be described in a single detailed description. Of course, it is certainly within the scope of the invention to include additional adjustable tension applicators and/or to vary the design of each adjustable tension applicator as desired.

In order to better understand the mechanical structures and operation of each of the first and second adjustable tension applicators 18 and 20, more particular reference is made to FIGS. 2 and 2A, which are cross-sectional views of second adjustable tension applicator 20 taken along line 2—2 in different stages of applying tension. Cross-reference to FIG. 1 may also be helpful in understanding the interplay between the first and second adjustable tension applicators 18 and 20 and their mechanical structures. Each of the first and second adjustable tension applicators 18 and 20 includes a cylinder block or module 22 and a tensioning piston 24 partially disposed within the cylinder module 22. The cylinder module 22 and tensioning piston 24 are able to slide relative to each other, as will be described more fully below.

In order to attach or otherwise secure each of two sets of looped sutures respectively attached to each of two soft tissue strands, each tensioning piston 24 further includes a suture attachment wheel 26 attached by means of an axle 28 to the tensioning piston 24. The suture attachment wheel 26 is able to rotate, and thereby self-adjust, after looped sutures have been tied and looped around the suture attachment wheel 26. This ability of the suture attachment wheel 26 to rotate ensures that equal tension is applied to each side of the looped suture. This, in turn, equalizes the tension applied to each end of a looped tissue graft strand. It will be appreciated, however, that other attachment means for attaching sutures or an end of a tissue graft to the tensioning piston 24 are within the scope of the invention, including slots, posts, holes, ridges, and the like (not shown).

In order to gauge the amount of tensile load being applied by each of the tensioning pistons 24 to its respective soft tissue graft strand, or group of strands, a tension post 30 attached to the tensioning piston 24 is provided, which extends through, and freely moves within, a tension indicator slot 32 within the cylinder module 22. As will be discussed below, the magnitude of the tensile load being applied to the soft tissue graft strand at any given time will be related to the relative distance that the tension post 30 has moved relative to the cylinder module 22. In actuality, because the tensioning piston 24 is essentially immobile due to the countervailing tension applied by the corresponding soft tissue strand, it is the cylinder module 22 and its associated tension indicator slot 32 that will typically move relative to the tension post 30 as the tensile load applied to the soft tissue graft is increased (Compare FIGS. 2 and 2A). Regardless of which element actually moves, the location of the tension post 30 relative to the tension indicator slot 32 provides the surgeon with a visual indicator of the amount of tensile load being applied by each adjustable tension applicator 18 and 20 to its respective soft tissue graft strand(s) at any given time. In order to provide a more accurate way of determining the exact load being applied, graduations 33 may be provided on the cylinder module 22 at or near the tension indicator slot 32. The graduations 33 may provide any desired measuring standard, such as metric (e.g., Newtons) or English units (e.g., pounds), as well as any desired level of precision.

In order to adjust the amount of tension applied by each adjustable tension applicator 18 or 20, a mechanism for moving the cylinder module 22 either towards or away from the tensioning piston 22 is provided. As seen in FIGS. 2 and 2A, each adjustable tension applicator 18 or 20 includes a tension adjustment knob 34 attached to a tension adjustment bolt 36 in threaded communication with the cylinder module 22. The tension adjustment bolt 36 passes through a pair of bolt holes 38 at the front and back ends of the tensioning block or module 16, respectively. The bolt holes 38 are not threaded and thus allow for free rotation of the tension adjustment bolt 36 without changing the location of the tension adjustment bolt 36 relative to the tensioning module 16. For ease of use, and to conveniently extend the tension adjustment knobs 34 behind or beyond the tensioning pistons 24, knob extenders 39 may be provided as shown in both FIGS. 1 and 2.

Beyond each of holes 38, each tension adjustment bolt 36 is suspended within a cylinder block guide cavity 40, which holds and guides the cylinder module 22 as it slides back and forth relative to the tensioning block 16 and the tensioning piston 24. More particular, a side tongue or extension 42 extending laterally from the bottom of the cylinder module 22 is able to slide back and forth within the cylinder block guide cavity 40. The side extension 42 of the cylinder module 22 further includes a threaded hole 44 through which passes, and which is in threaded communication with, the tension adjustment bolt 36, which includes corresponding threads 46. The interaction between the adjustment bolt threads 46 and the threaded hole 44 of the cylinder module 22 provides for fine, adjustable movement of the cylinder module 22 relative to the tensioning piston 24 as the tension adjustment bolt 36 is selectively rotated, such as by means of the tension adjustment knob 34.

The degree or magnitude of movement of the cylinder module 22 per revolution of the tension adjustment bolt 36 is, of course, dependent on the gauge of the threads 44 and 46. Increasing the number of threads 46 per unit of length on the adjustment bolt 36 and threaded hole 44 provides for smaller or finer movements of the cylinder module 22 per turn of the adjustment bolt 36. Likewise, decreasing the number of threads 46 per unit of length on the adjustment bolt 36 and threaded hole 44 provides for larger or coarser movements of the cylinder module 22 per turn of the adjustment bolt 36. One of ordinary skill in the art can select a thread gauge in order to provide for a desired magnitude of movement of the cylinder module 22 per turn of the adjustment bolt 36.

As seen in FIGS. 2 and 2A, the tensioning piston 24 further includes a first piston end 48 having a first diameter and a second piston end 50 having a second diameter that is smaller than the diameter of the first piston end 48. A biasing spring 52 is circumferentially disposed around the second piston end 50 and makes abutment with an internal end face 54 of the first piston end 48. As better seen in FIG. 1, the tensioning piston 24 also includes a longitudinal guide pin hole 56 through which a guide pin (to be discussed hereinafter) can pass, if necessary, during attachment of the tensioning device 10 to the patient's limb. The tensioning piston 24 also includes an attachment hole 58 into which the tension indicator pole 30, is mounted.

As stated above, the tensioning piston 24 is slidably disposed within the cylinder module 22. As more particularly seen in FIGS. 2 and 2A, the cylinder module 22 includes an internal cylindrical hollow 60 having a diameter that is complementary to the diameter of the first piston end 48 so as to allow for slidable passage of the first piston end 48 therethrough as the cylinder module 22 is moved either towards or away from the tensioning piston 24. The cylinder module 22 further includes a smaller diameter end hole 62 sized so as to allow for slidable passage of the smaller diameter second piston end 50 therethrough as the cylinder module 22 is moved either towards or away from the tensioning piston 24. The biasing spring 52 that is circumferentially disposed around the smaller diameter second piston end 50 of the tensioning piston 24 makes abutment with an internal end face 64 of the internal cylindrical hollow 60 at the junction with the end hole 62.

Thus, the biasing spring 52 is maintained within the length or volume defined by the internal end face 64 of the internal cylindrical hollow 60, on one end, and the internal end face 54 of the fist piston end 48 of the tensioning piston 24, on the other end. In this way, the biasing spring 52 becomes compressed as the cylinder module 22 is moved towards the tensioning piston 24 (as seen in FIG. 2A), thereby increasing the compressing force applied by the biasing spring 52 onto the tensioning piston 24, which is essentially equal in magnitude to the tensile load applied by the tension piston 24 onto the soft tissue graft attached thereto, such as by way of tissue graft attachment sutures.

The foregoing tensioning system is merely exemplary and not limiting. Although the tensioning piston 24, cylinder module 22 and biasing spring 52 are configured so as to progressively compress the tensioning spring in order to apply increasing force to a soft tissue graft, it would certainly be within the scope of the invention to provide a configuration or alternative tensioning system in which a biasing spring were instead progressively elongated in order to apply increasing force to the soft tissue graft.

In order for the foregoing tensioning system 12 to be conveniently used to independently tension a pair of soft tissue grafts, the tensioning system 12 is advantageously attached to the patient's limb (e.g., the leg below the knee) by means of the limb attachment system 14. As seen in FIGS. 1, 2 and 2A, the limb attachment system 14 includes a limb attachment block or module 66 that is matable with the tensioning block or module 16. In this way, once the attachment module 66 has been attached to the patient's limb, the tensioning system 12 can be conveniently and easily attached to the limb attachment system 14.

Figure 3A:
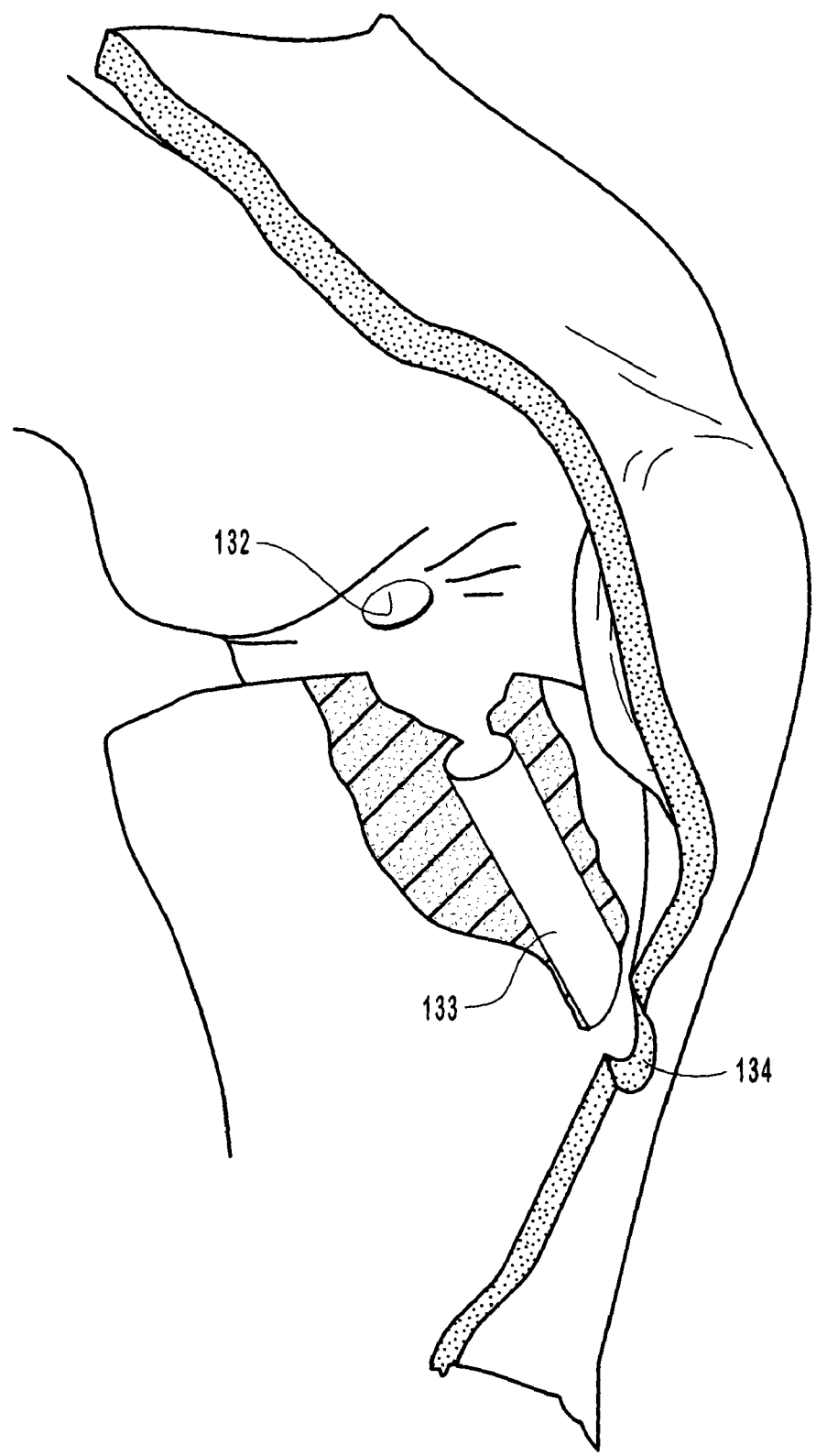
Figure 3B:
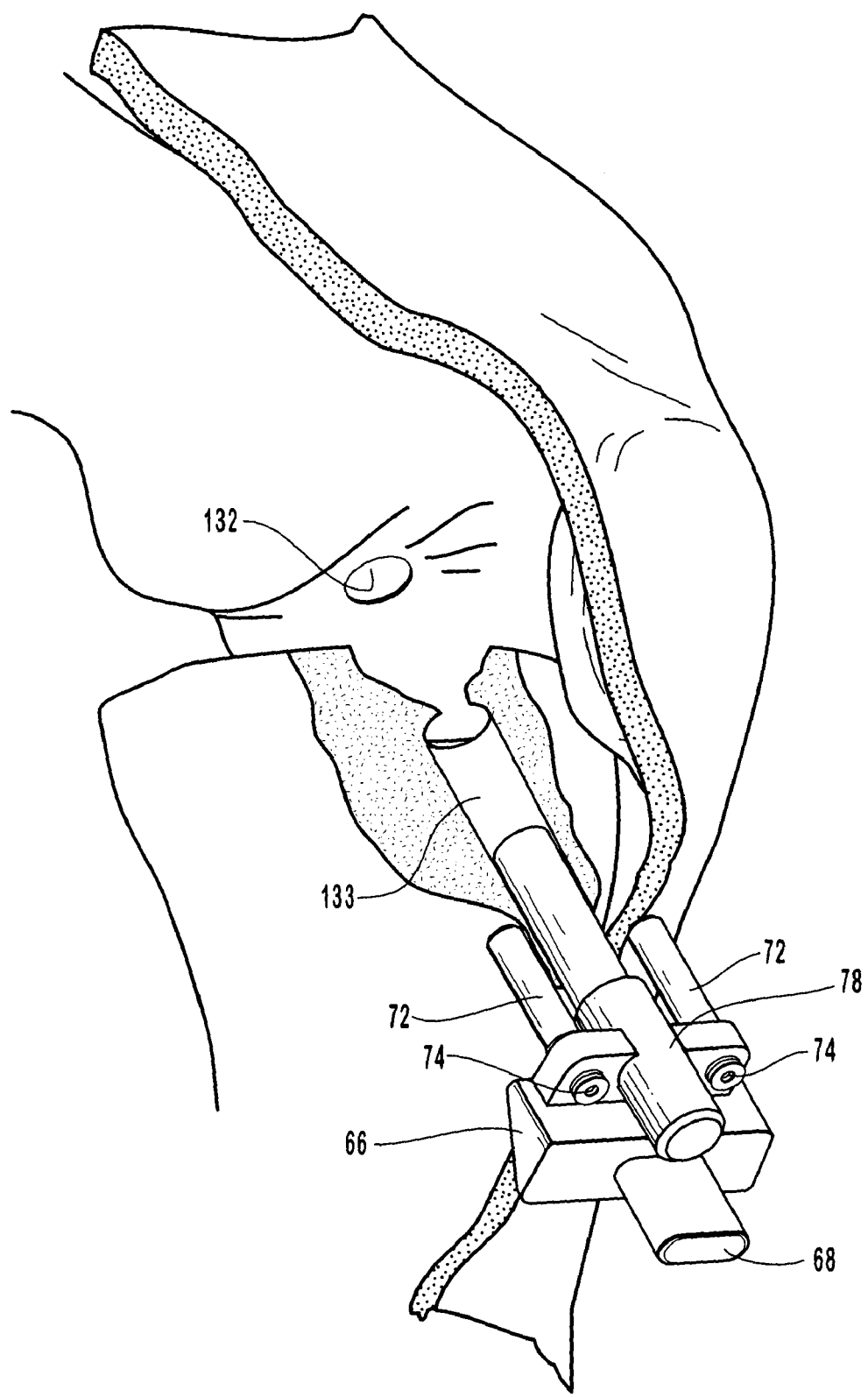
Figure 3C:
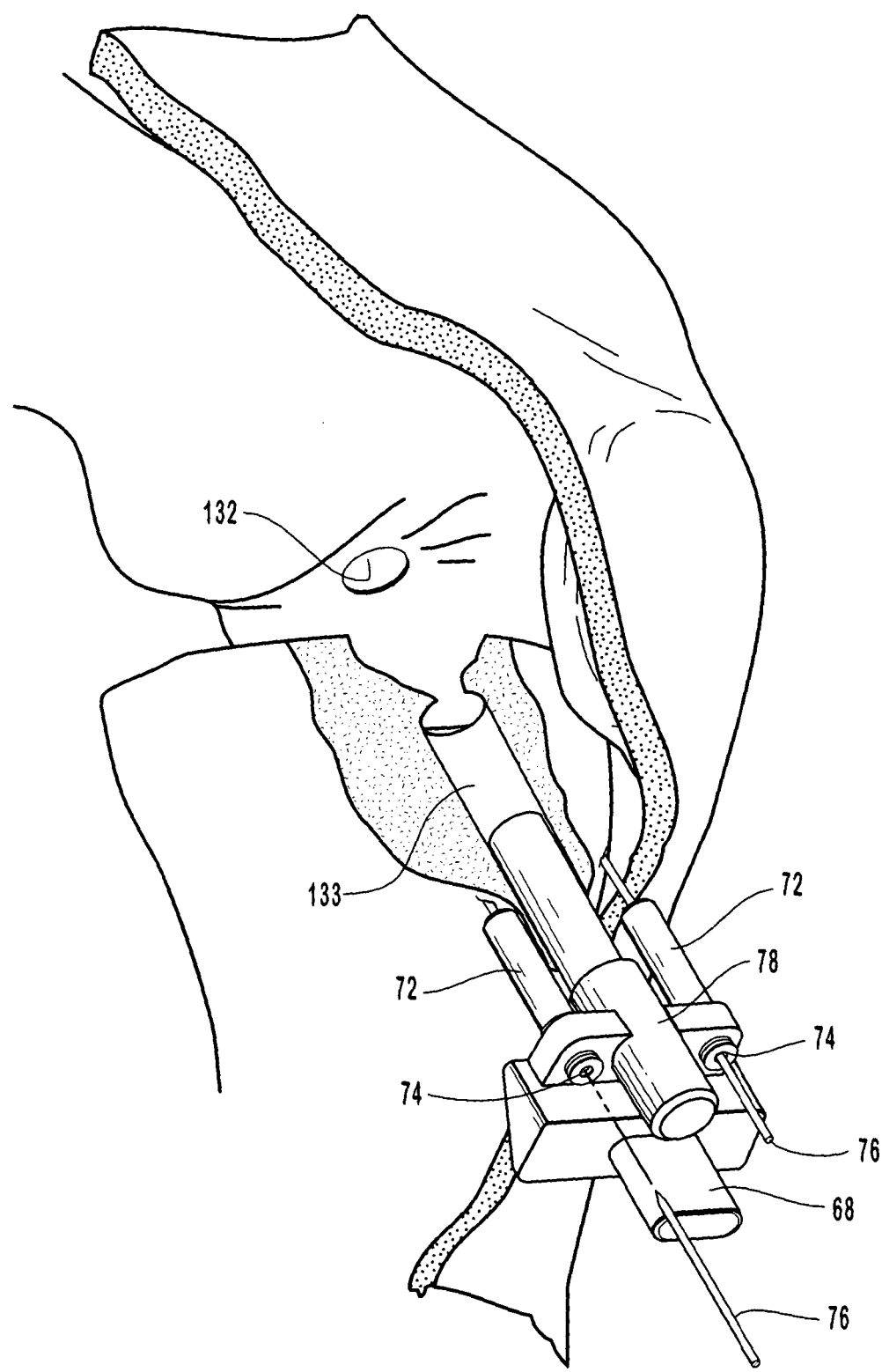
Figure 3D:
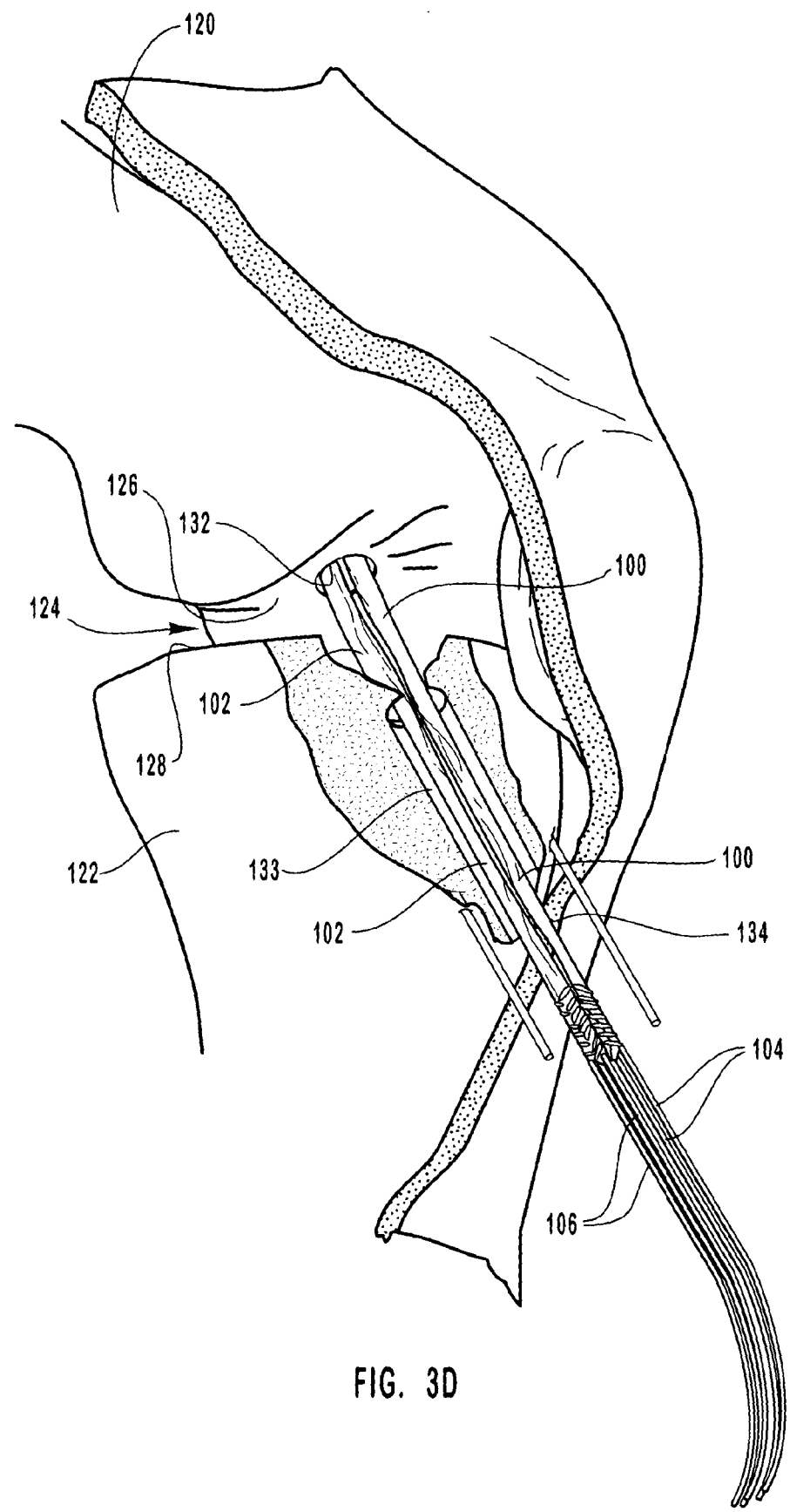
Figure 3E:
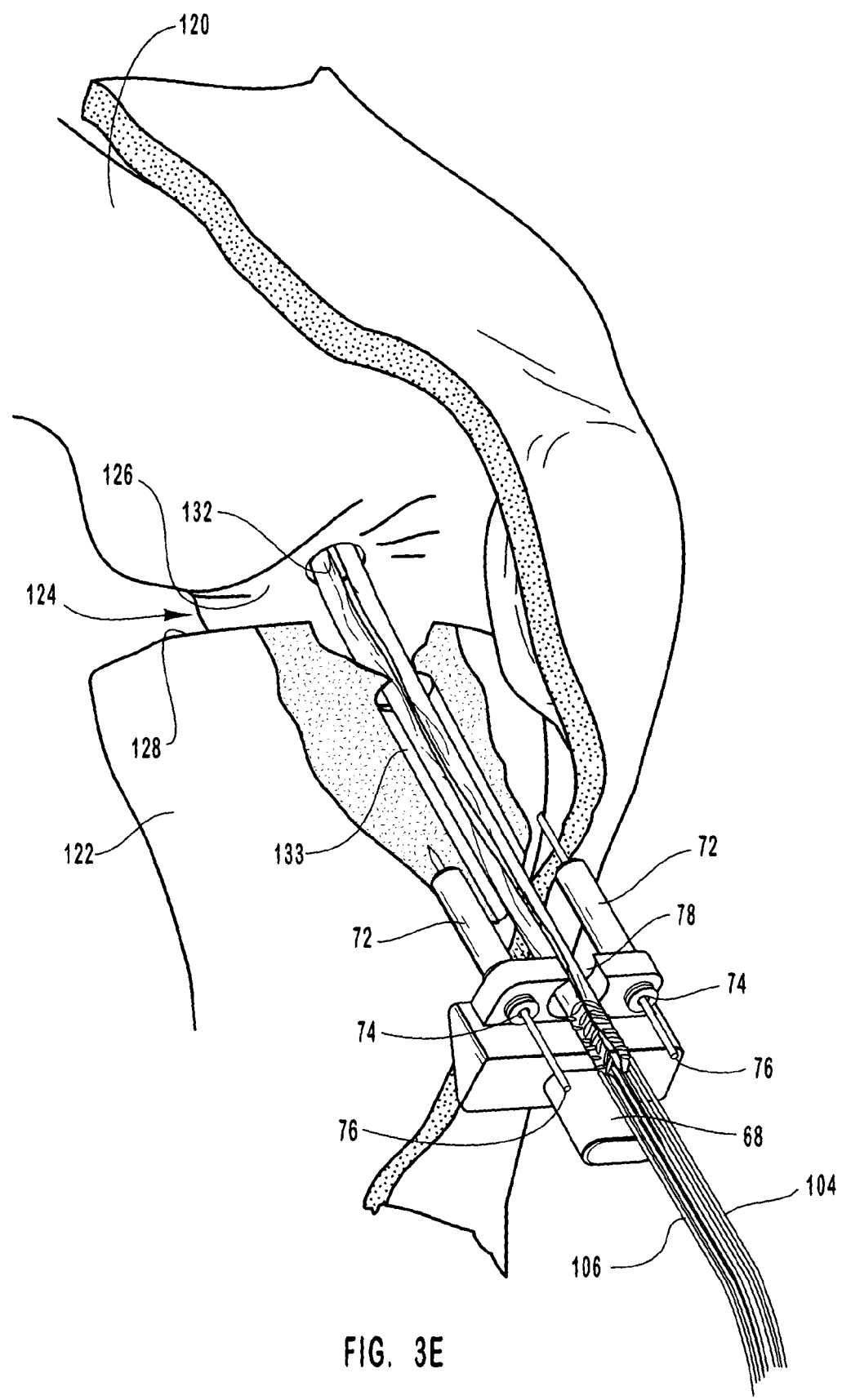
Figure 3F:
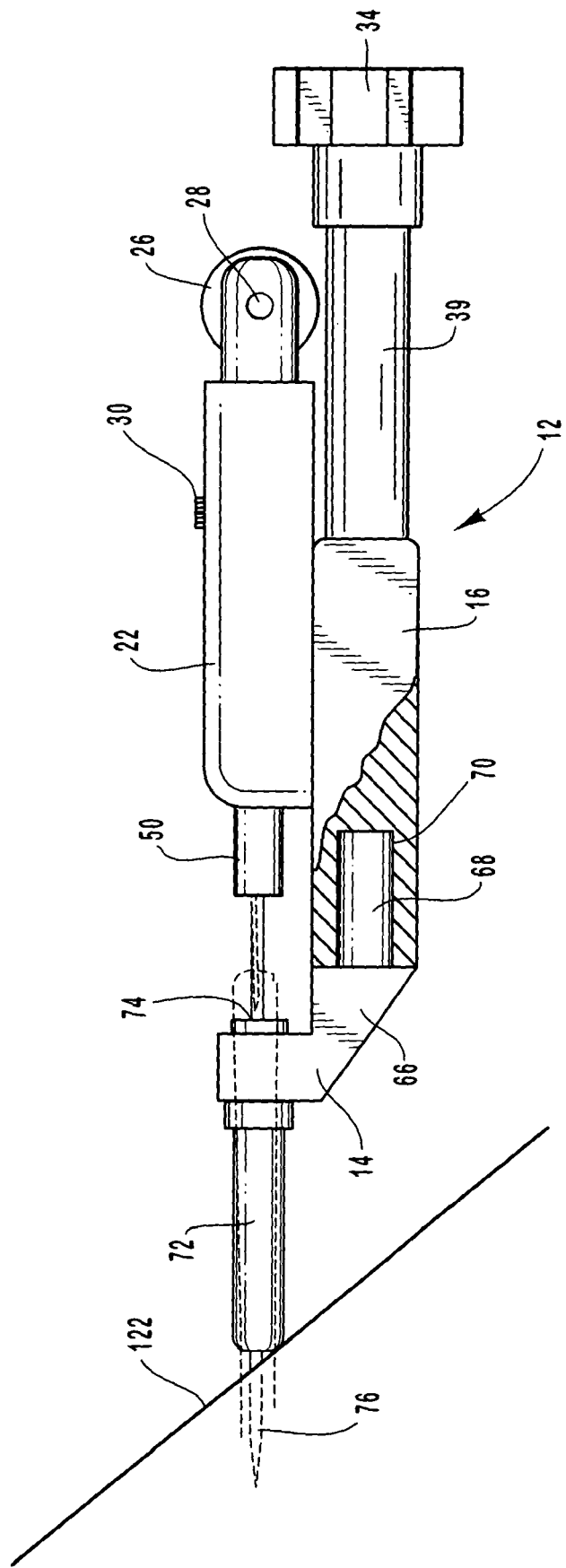
Figure 3G:
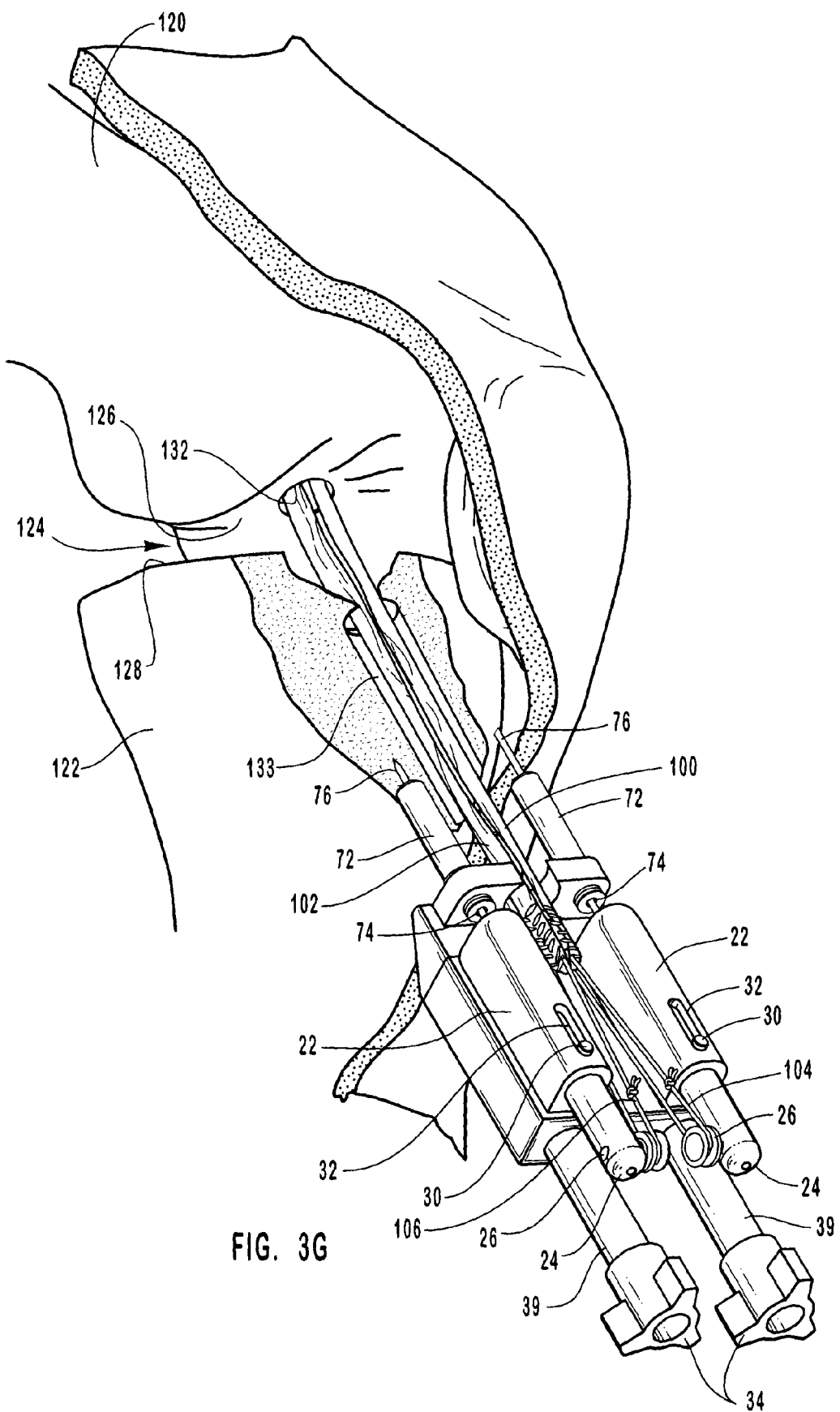

As shown more particularly by comparing FIGS. 3B and 3G, the limb attachment module 66 may include a mating tongue 68 or other protrusion or mechanical feature (not shown) that is able to mate with a corresponding mating hole 70 in the tensioning block or module 16 (FIG. 3F) or other corresponding mechanical feature (not shown). Of course, the features may be reversed so that the mating tongue protrudes from the tensioning module 16 and so that the mating hole is formed within the limb attachment module 66. One of ordinary skill in the art, in light of the teachings herein, will readily appreciate that virtually any desired mechanical mating system may be employed so long as they provide for selective attachment and detachment of the tensioning system 12 from the limb attachment system 14. Of course, it is certainly within the scope of the invention to provide tensioning apparatus in which both the tensioning system 12 and the limb attachment system 14 comprise a single, non-modular unit.

As more easily seen in FIGS. 1, 2 and 2A, the limb attachment module 66 further includes a pair of pin guides 72, each having a longitudinal guide pin hole 74 therethrough sized so as to accommodate a guide pin 76 (FIG. 3C). When in use, the guide pins 76 are driven, drilled or otherwise pushed into the bone of the patient's limb (as discussed more fully below) in order to slidably attach the limb attachment module 66 to the patient's leg or other limb. In order to utilize the limb attachment module 66 as a template during proper placement of the guide pins 76, the limb attachment module 66 may first be attached to the patient's limb by means of a temporary guide post 78, which is advantageously sized at one end so as to slide into a corresponding hole in the patient's tibia or other bone (FIG. 3B). The other end of the guide post 78 is advantageously sized so as to pass through a corresponding guide post hole 80 in the center of the front end of the limb attachment module 66. When pressed into the hole in the patient's tibia or other bone, the guide post 78 advantageously holds the limb attachment module 66 in place during placement of the guide pins 76 into the person's tibia or other bone.

Once the guide pins 76 have been properly placed, the guide post 78 may be removed so as to allow access to the holes within the tibia and femur. Once the guide pins 76 have been attached to the bone, the limb attachment module 66 can be conveniently slid on and off the guide pins 76 as desired. Even though the limb attachment module 66 is only slidably connected to the guide pins 76, the tensioning device 10 is held in place against the patient's limb by the countervailing tension exerted by the soft tissue graft being tensioned. When conditioning and pre-tensioning of the soft tissue graft has been completed, the soft tissue graft is first secured to the tibia or other bone and then detached from the tensioning device 10. At this point, the tensioning device 10 can be slidably removed from the guide pins 76, which are then also removed from the patient's limb.

Notwithstanding the foregoing, one will readily appreciate, in view of the disclosure herein, that the inventive devices according to the invention are not limited to any particular mechanism for performing the individual and separate tasks of independently tensioning a plurality of soft tissue grafts. The mechanisms described herein are but illustrative and exemplary. For example, the tension loading and lead measuring functions could alternatively be provided by a variety of simple scales, such as tension springs, compression springs, torsion springs or electronic transducers. In addition a variety of electronically actuated and measured tensioning devices are certainly within the scope of the invention so long as they are capable of independently tensioning separate soft tissue grafts. Examples include a strain gauge, a rotary gauge, an LVDT and the like.

In addition to conditioning and pre-tensioning individual strands, or separate groups of strands, of a multiple-stranded soft tissue graft, the tensioning device can potentially be used to monitor isometry and measure tension in a single strand of a soft tissue graft. The current design could also be altered in order to incorporate additional adjustable tension applicators that can exert and measure tension in as many stands as a surgeon might choose to include in the soft tissue graft.

An advantage of the inventive tensioning device is the ability to pre-condition the graft after implantation at one end but before fixation of the other end. In the case of an ACL reconstruction procedure, because the soft tissue graft is attached to the tibia near the fixation site, the graft can be tensioned and conditioned by repeatedly flexing and extending the patient's knee under load to remove any laxity or looseness in the graft construct.

The proposed device is advantageously free-standing on the tibia, which can free the surgeon's hands to set knee flexation angle and fix the distal end of the graft while monitoring tension. The device is also able to sustain a desired tensile load on the graft for static tensile loading that will help stretch and condition the graft before final fixation.

An additional feature of the present invention is the understanding of how to independently conditioning and pre-tensioning each of two or more of the strands, or groups of strands, of a multiple-strand soft tissue graft (e.g., a ham string tissue graft), and why to do so aids the long-term strength and stability of the repaired joint. Thus, it should be understood that the inventive methods disclosed herein may be carried out using any device, either known or which may be developed in the future, that is capable of performing the inventive steps of independently conditioning and pre-tensioning each of two or more strands of a multiple-strand soft tissue graft. Therefore, although the use of the tensioning device 10, as more fully described herein, is described, its use is merely illustrative and is not intended as a limitation as to the types of apparatus that may be used to perform the inventive methods disclosed herein.

Reference is now made to FIGS. 3A–3L. In a preferred method for carrying out joint repair procedures according to the present invention, two or more strands comprising the soft tissue graft are harvested from the patient, such as from the ham strings or patellar tendon. In a preferred embodiment, the semitendinosus and gracillis are harvested from the patient's body. As shown in FIG. 3D, the soft tissue graft may comprise a first soft tissue strand 100 and a second soft tissue strand 102 (FIG. 3D). At some point during the procedure, first graft attachment sutures 104 are attached to the free end of the first soft tissue strand 100 and second graft attachment sutures 106 are attached to free end of the second soft tissue strand 102. In the case of a looped tissue graft, there will be a pair of free ends on each tissue graft strand.

Either before or after the graft attachment sutures 104 and 106 have been attached to their respective soft tissue strands 100 and 102, the ends of the soft tissue strands 100 and 102 opposite the free ends (or the ends where tension is to be applied) are attached at an appropriate location on the patient's bone comprising one of the bones of the joint. In the case of surgery to repair a knee joint (e.g., reconstruction of the anterior cruciate ligament), the ends of the soft tissue strands 100 and 102 opposite the tensioning ends are preferably attached to the femur 120. At the end of the conditioning and pre-tensioning procedure, the free tensioning ends of the soft tissue strands 100 and 102 are secured to the tibia 122.

As seen in FIG. 3D, the knee joint 124 comprises, and is defined by, the intersection of the femur 120 and the tibia 122, more particularly the enlarged end 126 of the femur 120 and the enlarged end 128 of the tibia 122. The enlarged end of 128 of the tibia is generally complementary in size and shape to the enlarged end 126 of the femur 120. The enlarged ends 126 and 128 are each covered with cartilage in a healthy knee to provide smooth, flexible joint surfaces. (For simplicity, we shall hereinafter refer only to the femur 120 and the tibia 122.) The knee joint 124 also includes surrounding connective tissue that holds the femur 120 and tibia 122 together so as to normally provide a stable and strong knee joint 124. One of the important components of this connective tissue is the anterior cruciate ligament 130 (ACL), which is a relatively short ligament connected at one end to a lower surface of the femur 120 and at the other end to the opposing surface of the tibia 122. A normal functioning ACL is vital in providing stability and strength of the knee joint 124, particularly for persons such as athletes who engage in physical activity that puts considerable stress onto the knee joint 124.

When the ACL is torn or ruptured, the knee becomes unstable and weak. During a traumatic event in which the ACL has been severely damaged, other surrounding connective tissue may also be seriously damaged. If left untreated, a severely damaged ACL may render a person partially or entirely crippled for life. Fortunately, a variety of strategies have been developed to "repair" or reconstruct the ACL, which typically comprises replacing the ACL with a soft tissue graft taken from a different part of the patient's body. In a preferred embodiment according to the present invention, a multiple-strand soft tissue graft, such as a pair of ham strings, may serve as an alternative "ACL" so as to restore the strength and stability of the knee joint 124.

In order to secure the soft tissue graft to either bone constituting the joint (e.g., the femur 120 and the tibia 122 of the knee joint 124), a hole is bored through each of the bones comprising the joint. In the case of reconstruction of the ACL 130 (as shown in FIG. 3A), a hole 132 is bored through the femur 120 and a corresponding hole 133 is bored through the tibia 122 using known surgical procedures (e.g., using a drill). In conjunction with this, an access hole 134 through the flesh in the vicinity of the hole 133 through the tibia 122 is provided. In the case where a tensioning device 10 is employed to condition and pre-tension the soft tissue graft, the joint is further prepared as follows to provide for removable attachment of the tensioning device 10.

As shown in FIG. 3B, the limb attachment block or module 66 is secured to the tibia 122 by first sliding the guide post 78 into the hole 133 through the tibia 122 and mating the guide post 78 with a corresponding hole in the attachment block 66. Thus attached, the attachment block 66 serves as a guide or template for proper placement of guide pins into the adjacent bone.

As seen in FIG. 3C, guide pins 76 may be driven, drilled or otherwise attached to the tibia 122 in the appropriate location using the limb attachment module 66 as a template, more particularly, the pin guides 72 and associated guide pin holes 74 of the limb attachment module 66. In one embodiment, the forward ends of the guide pins 76 to be driven into the bone may be provided with a tip having a cutting surface so as to be self-tapping and able to bore into the tibia 122 by means of a drill (not shown). Once both guide pins 76 have been secured to the tibia 122, the guide post 78 and limb attachment module 66 can be removed. The guide pins 76 may be trimmed if desired to a desired length (e.g., by means of a saw, diagonal cutters, or other cutting tool known in the art).

As shown in FIG. 3D, with the guide pins 76 in place following removal of the guide post 78 and limb attachment module 66, first and second strands 100 and 102 comprising the soft tissue graft may be inserted through the access hole 134 using known surgical techniques. The tensioning ends of the graft strands 100 and 102 are advantageously attached to first and second graft attachment sutures 104 and 106, respectively. The ends of the soft tissue strands 100 and 102 opposite the graft attachment sutures 104 and 106 are fed through the holes 132 and 133 of the femur 120 and tibia 122, respectively, and attached to the femur 120 using known surgical procedures (not shown). Examples of attachment devices include screws, pins, staples, posts and other anchor devices known and used in the art. Once the first and second soft tissue strands 100 and 102 have been passed through holes 132 and 133, securely mounted to the femur 120, and attached to first and second graft attachment sutures 104 and 106, respectively, they are ready for conditioning and pre-tensioning.

As shown in FIG. 3E, the limb attachment module 66 of the limb attachment system 14 is reattached to the guide pins 76 by sliding each of pin guide 72 over its respective guide pin 76 until the limb attachment module 66 makes abutment with the patient's leg. This may be performed before or after attaching the tensioning module 16 of the tensioning system 12 to the limb attachment module 66, which is performed by inserting the mating tongue 68 of the limb attachment module 66 through the mating hole 70 of the tensioning module 16. FIG. 3F shows an assembled tensioning device 10 attached to the tibia 122 and ready for use in conditioning and pre-tensioning a soft tissue graft.

As seen in FIG. 3G, the graft attachment sutures 104 and 106, which are attached to respective soft tissue graft strands 100 and 102, are attached to corresponding tensioning pistons 24. In this embodiment, each attachment suture 104 and 106 includes a pair of free ends that are tied together so as to formed looped sutures 104 and 106, which are in turn looped around corresponding suture attachment wheels 26. The suture attachment wheels 26, if allowed to freely rotate, equalize the tension that is, or will be, applied to the two sides of the looped sutures 104 and 106. The tensioning device 10 is now ready for use in separately and independently conditioning and pre-tensioning each of the first and second soft tissue strands 100 and 102.

Each tension adjustment knob 34 of first and second adjustable tension applicators 18 and 20 (FIG. 1) is separately operated as desired to independently apply a desired tensile load to each of first and second soft tissue strands 100 and 102. The magnitude of the tensile load being applied to each soft tissue strand 100 and 102 may be measured by the displacement of each tension indicator pole 30 relative to its respective tension indicator slot 32, particularly by referencing the location of each tension indicator pole 30 in relation to corresponding graduations 33 on the side of the corresponding tension indicator slot 32. It may be desirable in some cases to tension each soft tissue strand with the same tensile load. In other cases, particularly where the strands of the soft tissue graft have different cross-sectional thicknesses and/or stiffnesses, it may be necessary or desirable to applied different tensile loads to each soft tissue strand in order for each soft tissue strand to bear a load that is appropriately selected. In general, it is desirable for thicker graft strands to be conditioned and pre-tensioned using a higher tensile load. Conversely, thinner graft strands will advantageously be conditioned and pre-tensioned using a smaller load.

Figure 3H:
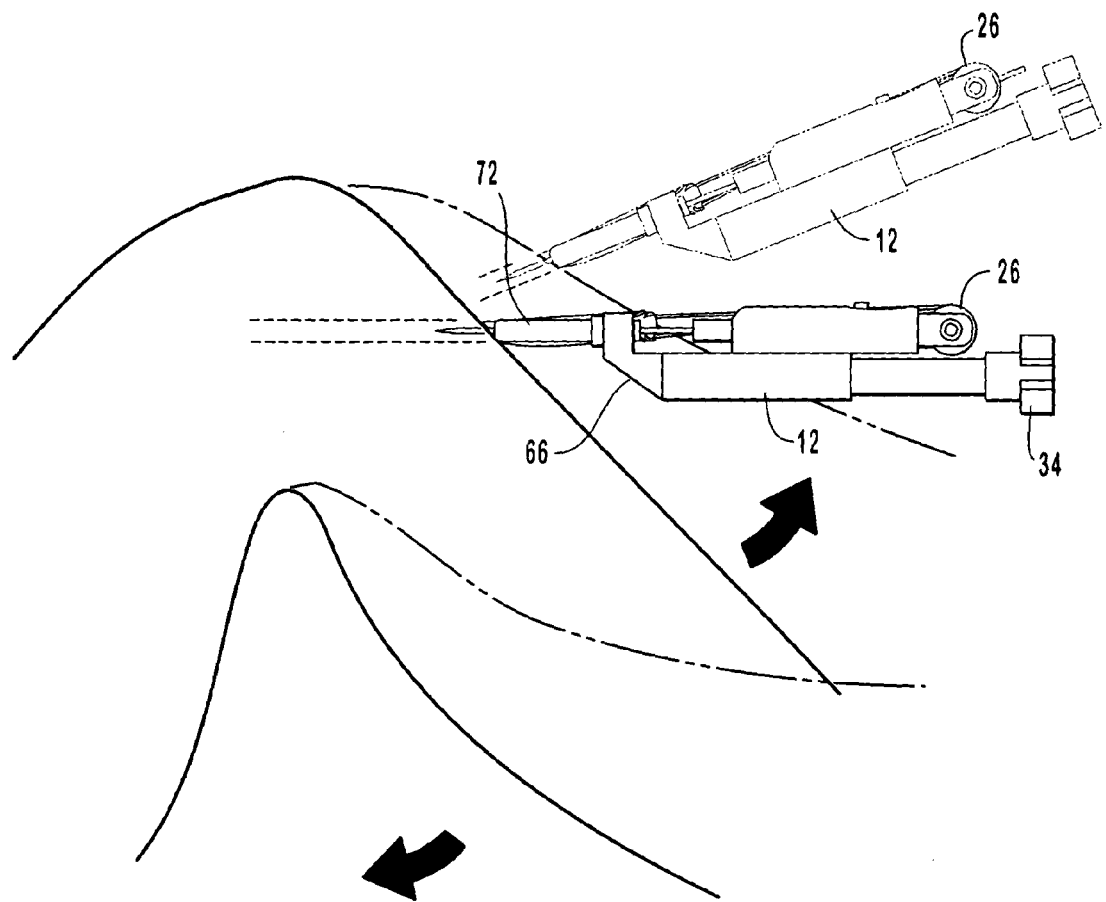

The process of "conditioning" the soft tissue graft is shown in FIG. 3H. First, an appropriated stress or tension is applied to each soft tissue strand. Thereafter, the leg or other limb is "cycled" by flexing and then extending the limb through a desired radial distance of, for example, 90°. If, after cycling, the soft tissue graft has loosened, or if the joint is not adequately stable, further adjustments to the tension adjustment knobs 34 may be required so as to increase the tensile load applied to one or more of the soft tissue graft strands 100 and 102 to ensure proper conditioning and pre-tensioning of the soft tissue graft. The process of alternatively tightening the tension adjustment knobs 34 and cycling the knee joint 124 may be repeated as needed until losses in joint strength and stability become negligible. At this point, proper conditioning and pre-tensioning of the individual strands of the soft tissue graft have been achieved.

In another embodiment, the soft tissue graft strands 100 and 102 are conditioned by applying an initial tension that is greater than the ultimate tension that will be born by each after the soft tissue graft is secured to the tibia 122. In this case, the conditioning process is performed after which the tension applied to each soft tissue graft strand 100 and 102 is individually decreased to an appropriate level. Applying excess tension initially does not harm the soft tissue graft and ensures that all play is reliably taken out of the system, both in terms of seating the sutures together with the free ends of the soft tissue graft strands 100 and 102 and pre-stretching each soft tissue strand 100 and 102 so that further stretching is eliminated or minimized during use of the repaired joint.

It should be understood that even though the tensioning pistons 24 are essentially immobile, with the cylinder modules 22 doing most, if not all, of the movement as the tension adjustment knobs 34 are tightened, some movement of the tensioning pistons 24 may be observed due to stretching of one or more of the soft tissue strands 100 and 102 and/or seating of the sutures 104 and 106. This movement, however, will typically be only a few millimeters or less. In any event, the amount of force that is independently applied to each of soft tissue strands 100 and 102 is independent of the movement of the tensioning pistons 24, thus negating any effect of unequal stretching or movement of the soft tissue strands 100 and 102. On the other hand, devices that attempt to condition and pre-tension the soft tissue graft with a single, undivided tensile load, are incapable of accounting for unequal stretching or movement of the soft tissue strands, thus resulting in unevenly conditioned and/or pre-tensioned strands. Thus, the methods and apparatus according to the present invention are a tremendous advancement in the art of preparing soft tissue grafts for use in joint repair surgery.

Figure 3I:
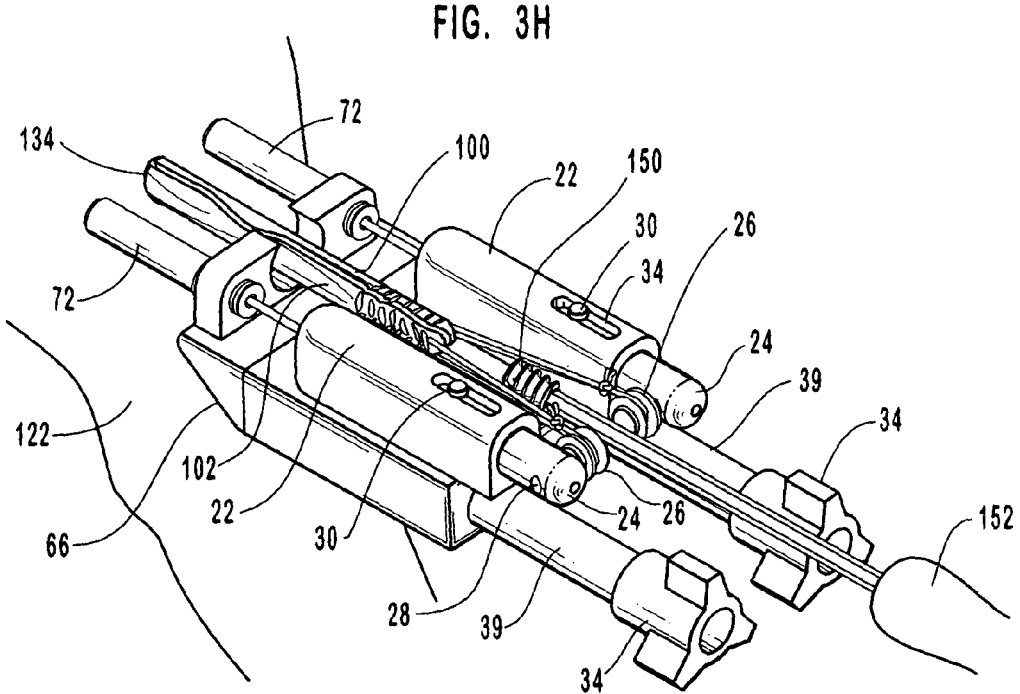
Figure 4A:
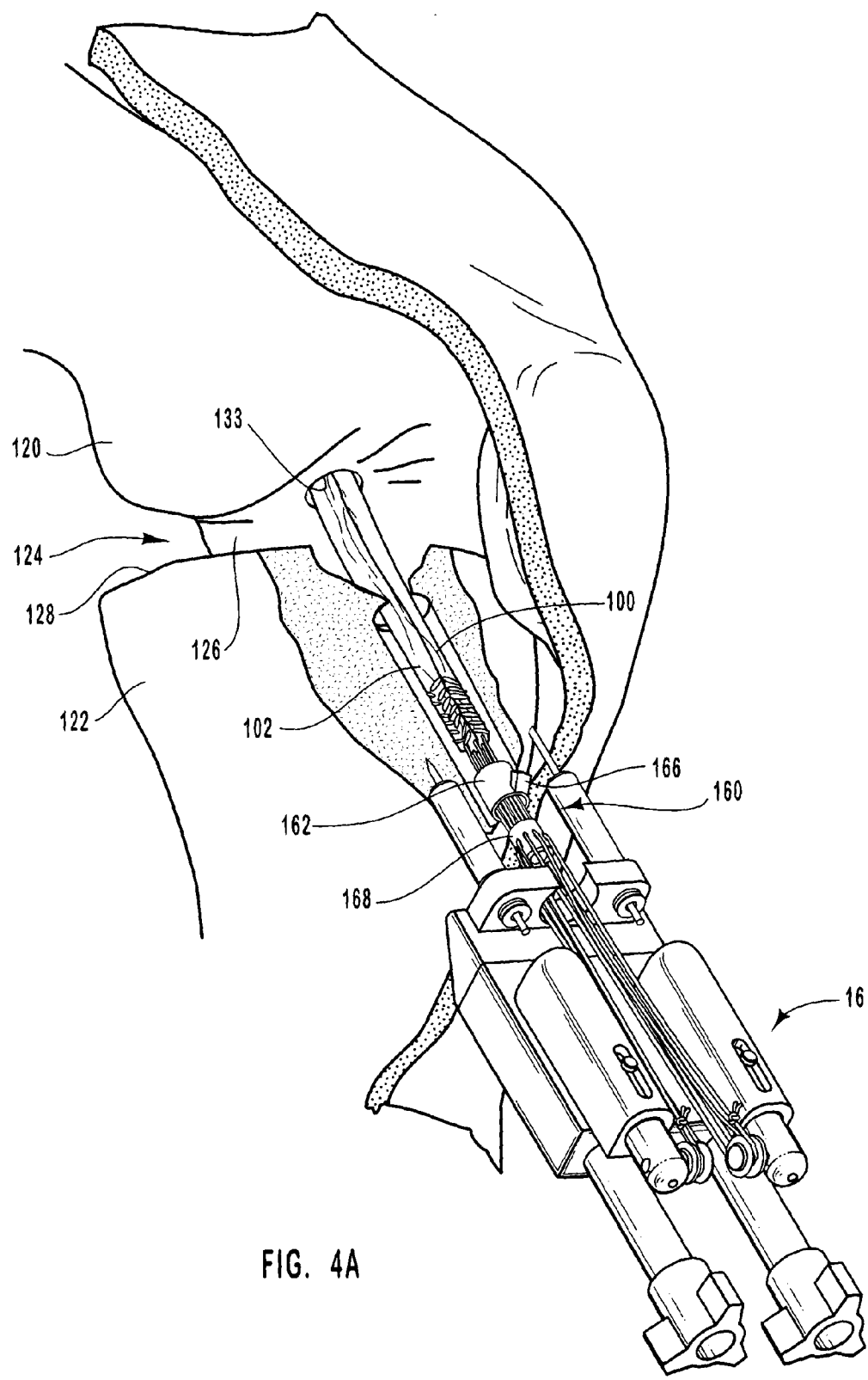
FIGS. 4A–4C illustrates an exemplary procedure in which a soft tissue graft is secured within a bone tunnel using an implantable anchor device.
Figure 4B:
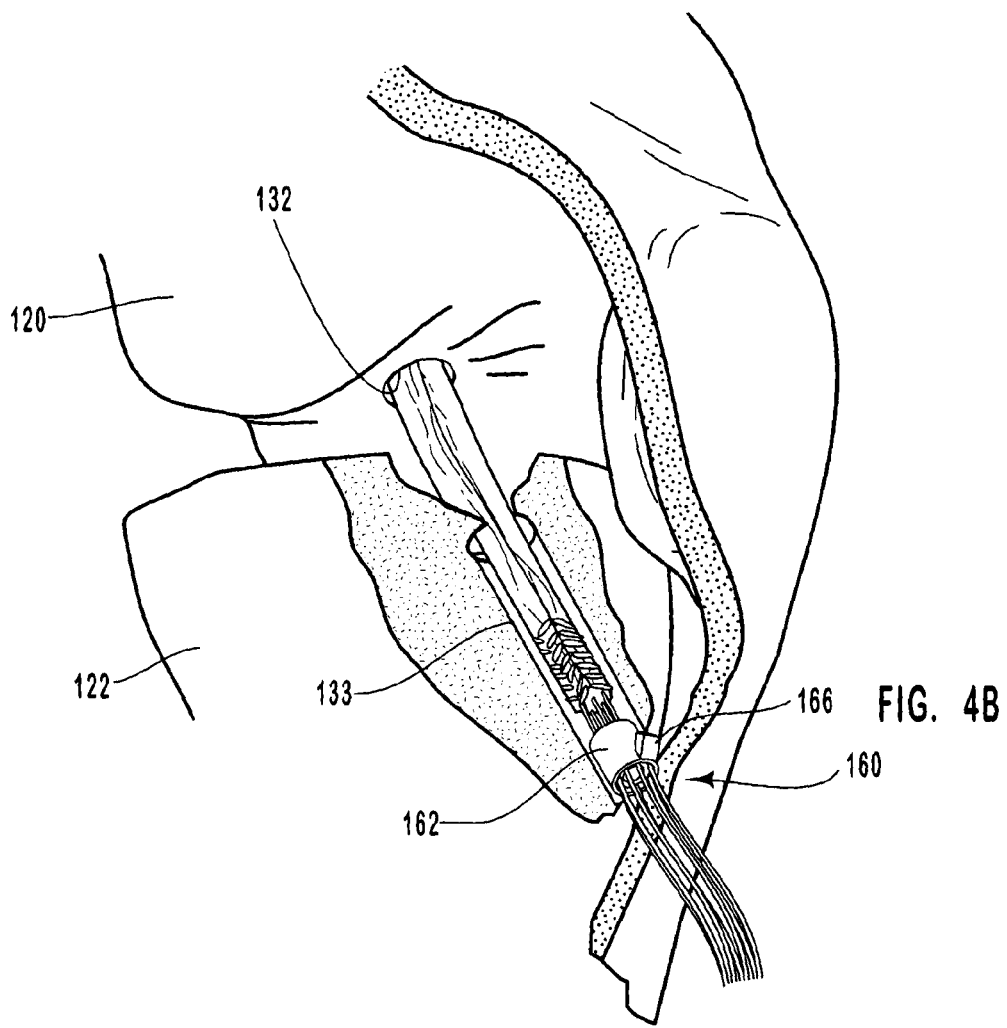
Figure 4C:
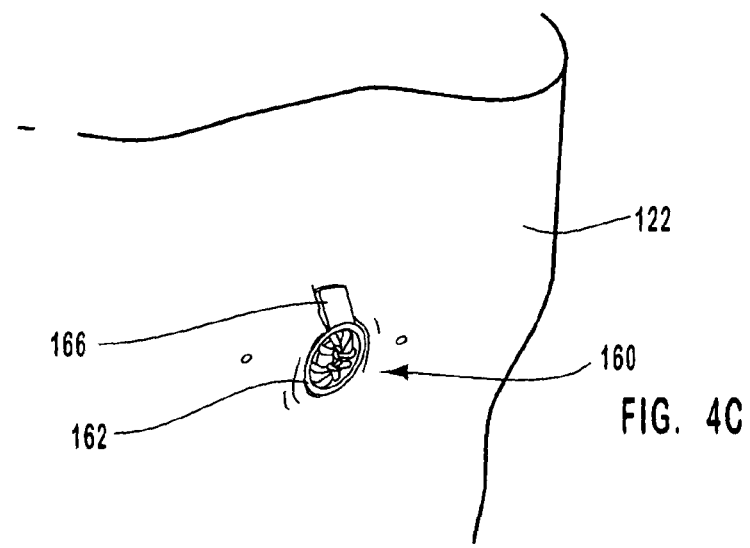

After the soft tissue strands 100 and 102 of the soft tissue graft have been properly conditioned and pre-tensioned, they are advantageously anchored or otherwise attached to the tibia 122 in order to maintain the desired amount of pre-tensioning. As shown in FIG. 3I, this may be accomplished, for example, by means of an interference screw 150. The interference screw 150 may be driven into the hole 133 in the tibia 122 by means of, e.g., a specially adapted screw driver 152. Alternatively, the graft may be anchored to the tibia 122 by means of an implantable anchor device 160, discussed more fully below.

After securing the soft tissue strands 100 and 102 of the soft tissue graft to the tibia 122 by means of the interference screw 150, the tensioning device 10 is removed by cutting or otherwise separating the sutures 104 and 106 from the suture attachment wheels 26 and then sliding the tensioning device 10 off of the guide pins 76 (FIG. 3J). Thereafter, the guide pins 76 are removed from the patient's tibia by known surgical procedures, such as by means of a "needle holder" (not shown) (FIG. 3K).

The ends of the soft tissue strands 100 and 102 of the soft tissue graft may thereafter be secured to the outside surface of the tibia 122 by standard surgical procedures, such as by means of a spiked washer, staple or post. FIG. 3K depicts a spiked washer 154 used to secure the remaining ends of the soft tissue graft strands 100 and 102 to the tibia 122. Finally, the end of the soft graft beyond the spiked washer 154 or other attachment means is trimmed to remove the graft attachment sutures 104 and 106 (FIG. 3L) using standard cutting apparatus (e.g., by means of a scalpel or surgical scissors, not shown).

Figure 5:
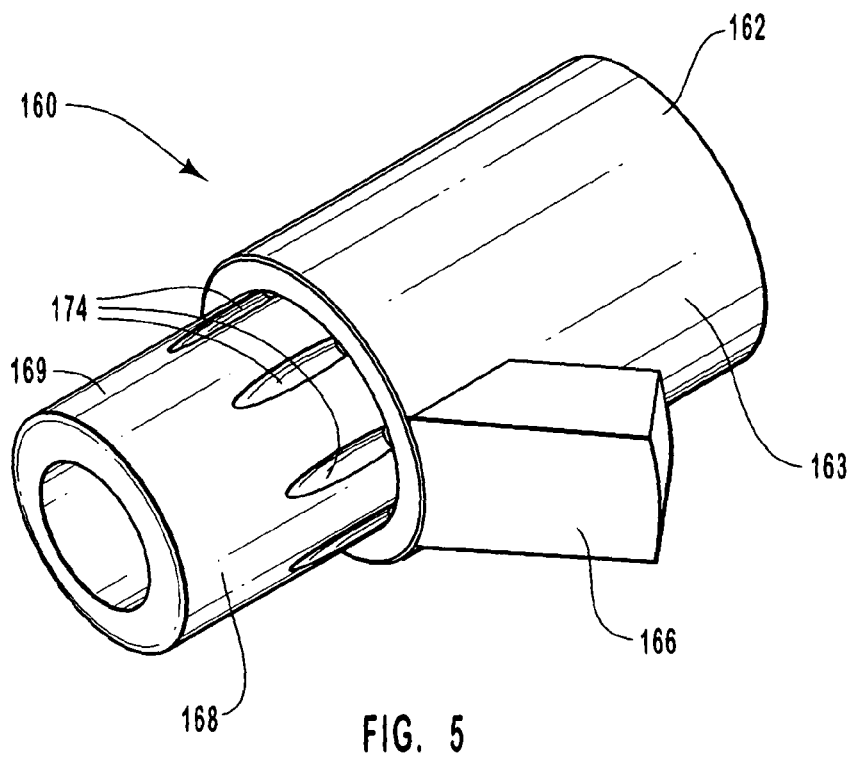
FIG. 5 is a perspective view of an anchor device according to the invention that allows for tensioning of sutures while in a non-deployed state and which locks the sutures upon deployment.
Figure 6:
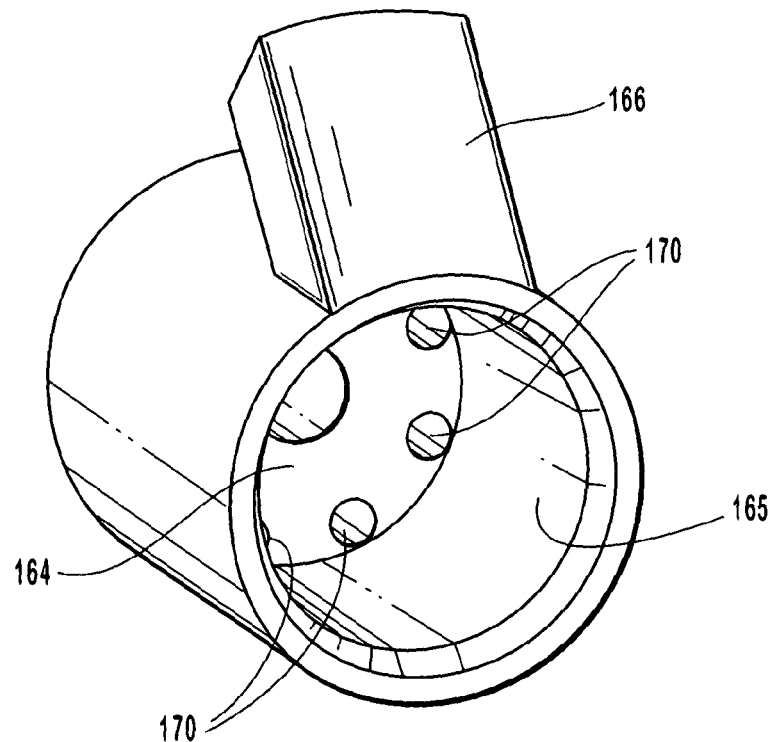
FIG. 6 is a perspective view of the outer sheath of the anchor device depicted in FIG. 5.
Figure 7:
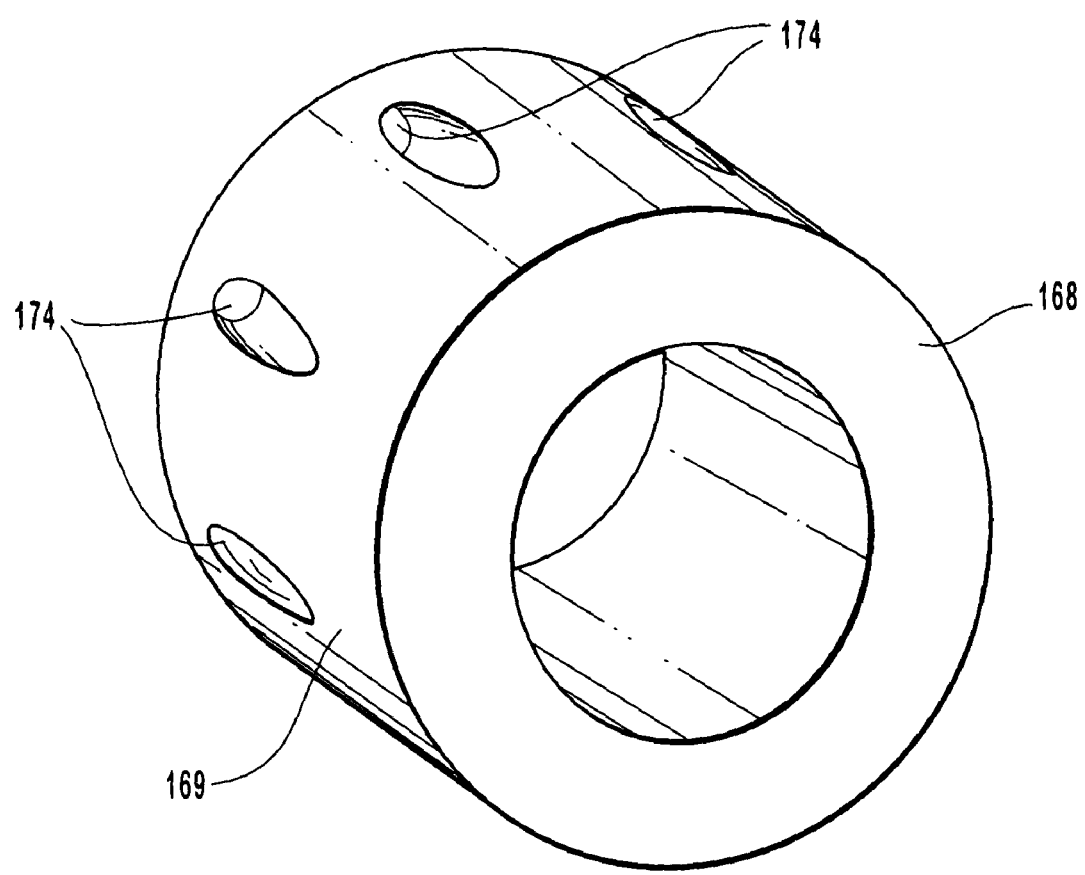
FIG. 7 is a perspective view of the locking core of the anchor device depicted in FIG. 5.

In an alternative embodiment (FIGS. 4–7), a novel implantable anchor device 160 according to the present invention may be employed to secure the soft tissue graft to the bone. As more particularly shown in FIGS. 5–7, the inventive anchor device 160 includes a generally cylindrical outer sheath 162 having a cylindrical outer wall 163, a generally cylindrical bore 164 therethrough (FIG. 6), defining an inner sheath wall 165, and a bone engagement lip 166. A corresponding locking core or shaft 168 (FIG. 7) is used to lock the sutures into place once the conditioning and pre-tensioning procedure has been completed.

The circumference of the outer wall 163 of the outer sheath 162 is selected to fit within a corresponding hole 133 bored through the tibia 122 or other bone. The bottom part of the outer sheath 162, or the part of the outer sheath 162 which faces the bone, includes a plurality of suture holes 170 disposed near the outer edge of the outer sheet 162 adjacent to the cylindrical outer wall 163. The suture holes 170 permit passage therethrough of individual suture strands attached to the strands of the soft tissue graft. When the anchor device 160 is placed into the hole 133 within the tibia 122 or other bone, the engagement lip 100 or other protrusion overlaps the outer surface of the bone, thus acting as a stop. The tension exerted inwardly by the soft tissue graft onto the sutures effectively pulls the engagement lip 166 or other protrusion against the bone, thereby reliably locking the anchor device 160 against the bone.

The locking core 168 is capable of sliding into and out of the outer sheath 162, but has a slightly tapered outer wall 169 so that it can form an increasingly tighter compression fit with the inner wall 165 of the outer sheath 162 as it is pressed or forced into the sheath 162. The locking core 168 is preferably hollow and includes suture passages 174 passing through the bottom edge nearest, and corresponding to, the suture holes 170 of the outer sheath 162. The suture passages 174 pass approximately longitudinally through the locking core 168 but at an angle so that they exit through the outer wall 169 of the locking core 168 rather than the top edge, or the edge facing away from the outer sheath 162. In this way, the sutures attached to the soft tissue graft will pass through the locking core 168 in a manner so as that, when the locking core is deployed, the sutures will be tightly pinched between the outer wall 169 of the locking core 168 and the inner wall 165 of the outer sheath 162. This pinching action prevents the sutures from slipping back into the bone hole, thus maintaining the desired tension on the sutures and associated soft tissue graft strands after conditioning and pre-tensioning of the individual graft strands, as described more fully above. Prior to deployment of the locking core 168, the sutures are free to slide between the outer sheath 162 and the locking core 168, which allows an appropriate tensioning apparatus, such as the tensioning device 10, to increase or decrease the tensile load applied to the soft tissue graft strands, as desired. The anchor device 160 can be used alone or in combination with other anchoring means known in the art.

Reference is now made to FIGS. 8–20, which illustrate a joint repair procedure utilizing alternative apparatus and methods of the invention. In this procedure, a non-modular tensioning device is used to tension the free ends of a pair of looped soft tissue graft strands, or graft bundles. A tissue graft measuring device is used to determine the diameter of each tissue graft bundle and also the composite graft comprising a plurality of graft bundles. A graft tension calculator is used to allocate the amount of tension applied to each graft bundle. The conditioned and pre-tensioned tissue graft is secured to the tibia using an interference screw. The procedure illustrated in FIGS. 8–20 will now be discussed in detail.

Figure 8:
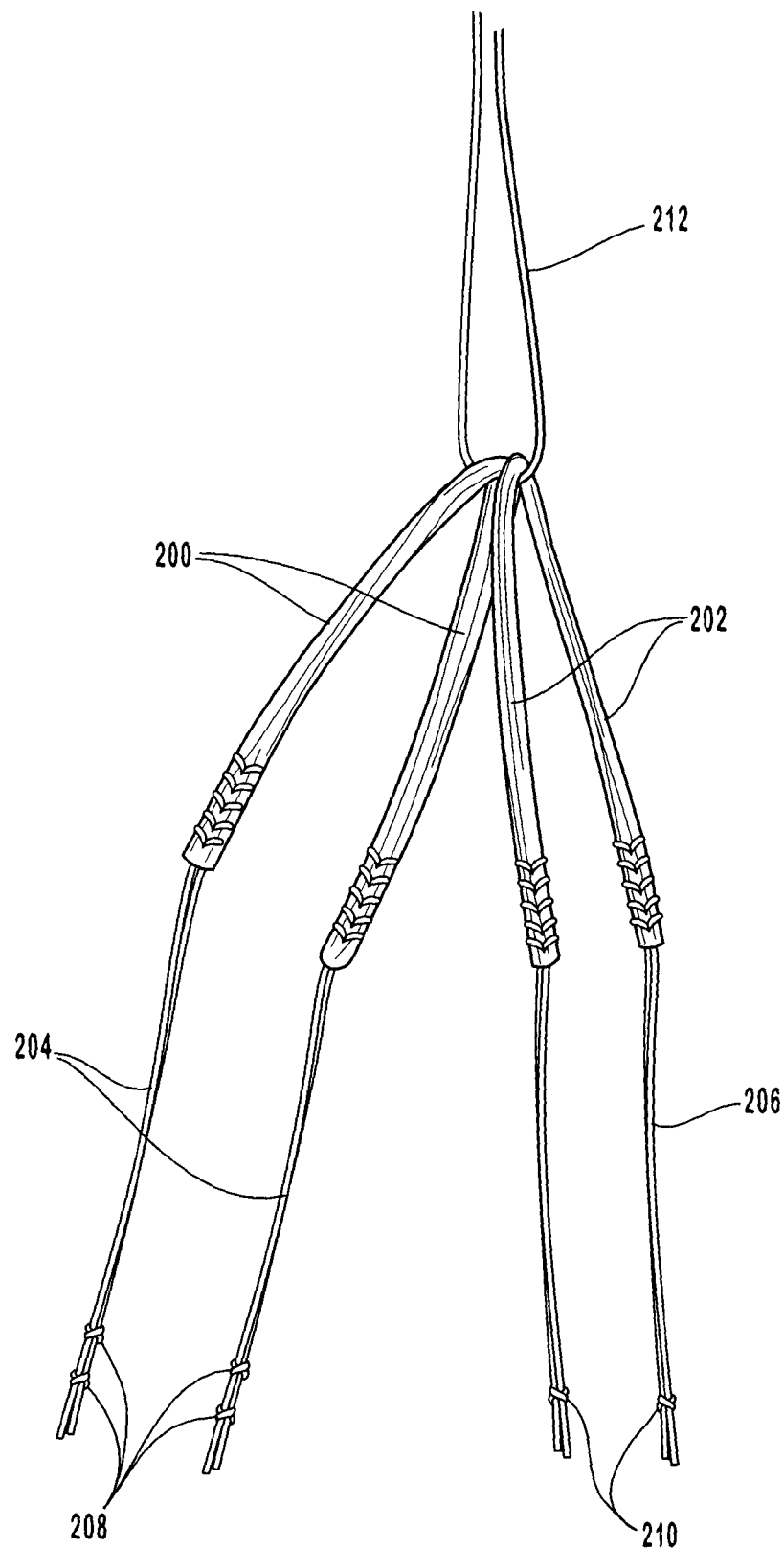
FIG. 8 depicts a pair of soft tissue graft strands that have been harvested from a patient and then doubled over to form looped tissue graft bundles.

FIG. 8 shows a pair of soft tissue graft strands that have been harvested from a patient's body using standard techniques, more particularly a semitendinosus tendon 200 and a gracillis tendon 202. The semitendinosus tendon 200 is slightly thicker in diameter than the gracillis tendon 202. For this reason, the tension applied to each will advantageously be individualized based on the relative diameters of each tendon. The result will be a proper load distribution across the entire multi-strand or composite graft. For most patients, the length of the semitendinosus tendon 200 and gracillis tendon 202 should be about 200 mm. Although the semitendinosus tendon 200 and gracillis tendon 202 are used in this example, it will be appreciated that the apparatus and methods disclosed herein are useful in conditioning and tensioning other soft tissue graft strands found in the body.

Preparatory to utilizing the semitendinosus tendon 200 and gracillis tendon 202 in a joint repair procedure, sutures are attached to the ends of each tendon 200, 202. As shown, suture strands 204 are whip-stitched to the free ends of the semitendinosus tendon 200, and suture strands 206 are whip-stitched to the free ends of the gracillis tendon 202. To assist in later distinguishing the semitendinosus sutures strands 204 from the gracillis suture strands 206, two knots 208 are advantageously tied in each semitendinosus sutures strand 204 and one knot 210 is advantageously tied in each gracillis suture strand 206. It will be appreciated that any number of knots, marking, mechanical feature or other distinguishing feature may be used to distinguish between the various suture strands. In order to facilitate the acts of measuring the diameters of the graft strands 200, 202 and then drawing looped graft strands 200, 202 through the prepared bone tunnels, they are advantageously looped around one or more graft passing sutures 212.

Figure 9B:
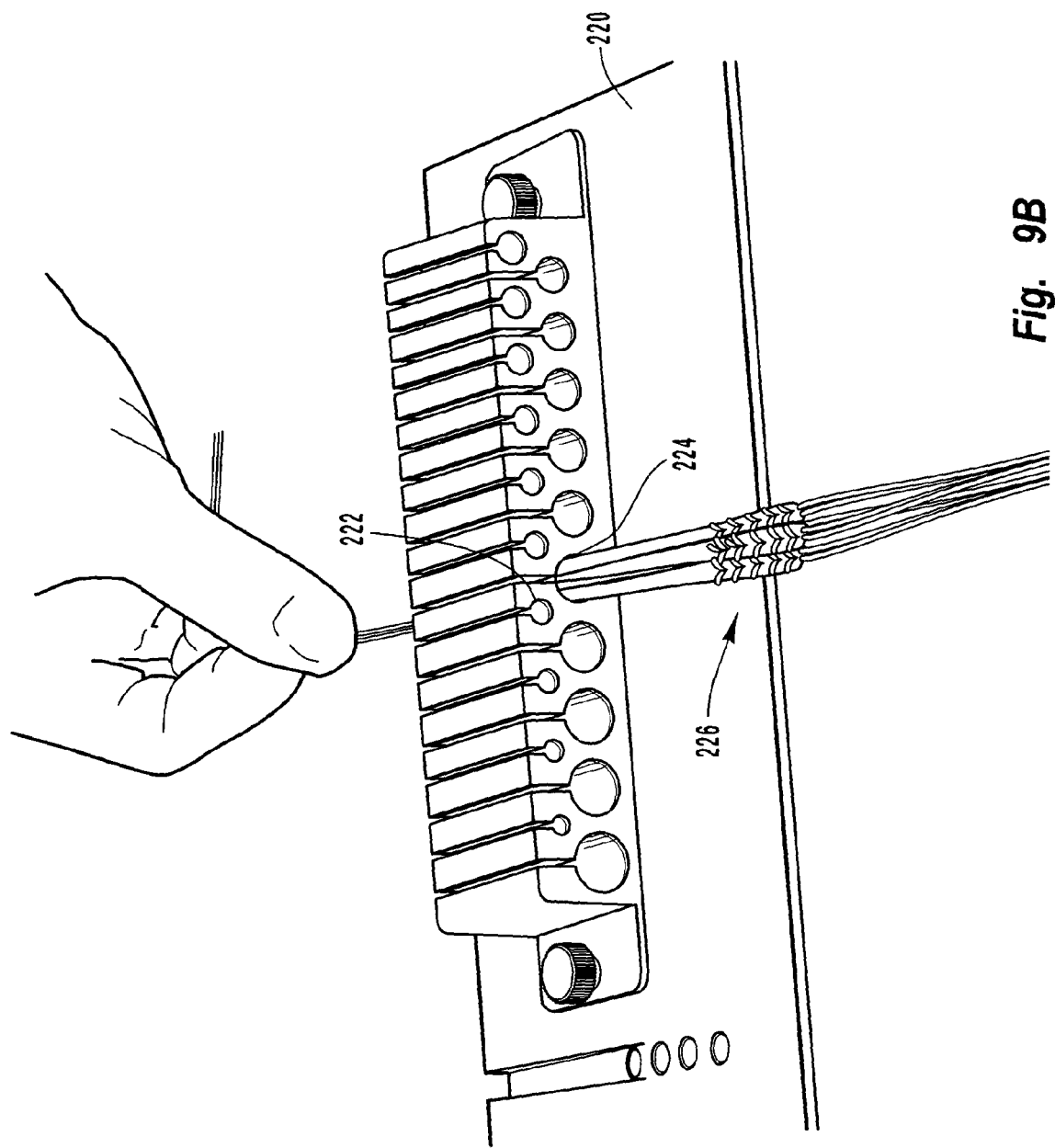

FIG. 9A depicts the act of measuring the diameter of the semitendinosus graft 200 after it has been looped or doubled over to form a graft bundle 201. This process is repeated for the graft bundle formed by looping or doubling over the gracillis graft 202. FIG. 9B depicts the act of measuring the overall diameter of the composite graft 226. In this embodiment, a graft sizing block 220 is provided that has smaller holes 222 of varying diameter for measuring the diameters of the individual graft bundle 201 and larger holes 224 of varying diameter for measuring the diameter of the composite graft 226. It will be appreciated that other measuring devices known in the art can be utilized to measure the relevant tissue graft diameters (e.g., rulers, calipers, and the like). The diameters of the individual graft bundle 201 or composite graft 226 are determined by pulling the composite graft 226 or graft bundle 201 through one or more holes 222, 224 until a good fit occurs. The diameter measurements will assist the surgeon in selecting an overall tensile load to be applied to the composite graft 226 and apportioning the overall tensile load between each graft bundle.

Figure 10:
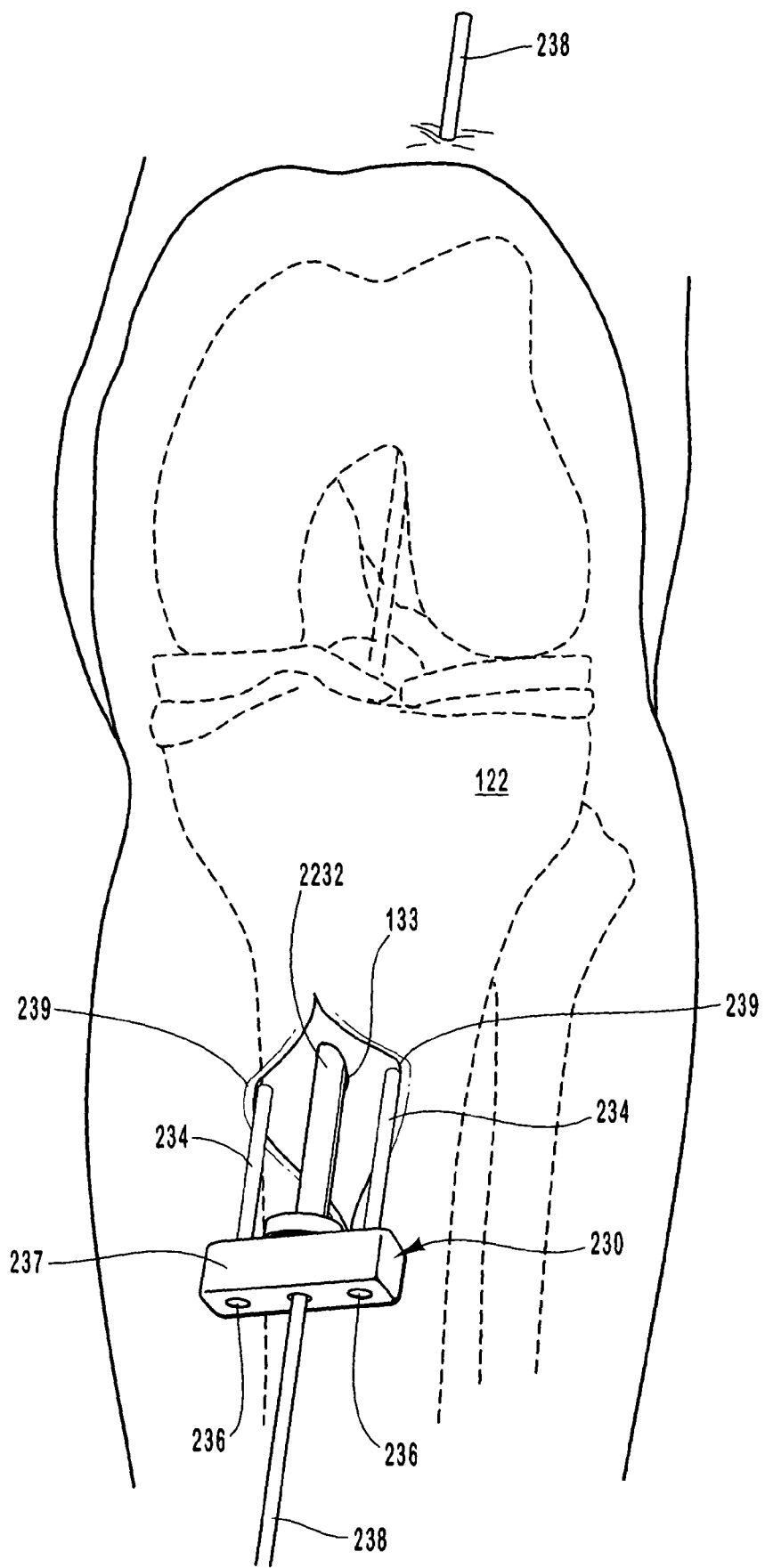
FIG. 10 show a joint to be operated on and a drill guide used to position guide pins that are used to position a tensioning device according to the invention.

In a surgical procedure for repairing the ACL, appropriately-sized tunnels are formed in both the femur and tibia, as described above and illustrated in FIG. 3A, using known methods. Once the tunnels have been formed, guide pins can be inserted into the tibia for later attachment of a tensioning device. As shown in FIG. 10, a drill guide 230 can be employed in order to provide a template for inserting guide pins into the tibia 122. The drill guide 230 advantageously includes a central guide post 232 for insertion into the tibial bone tunnel 133, a pair of spaced-apart hollow pin guides 234 used to insert guide pins into the tibia 122, and corresponding drill guide apertures 236 through a bridge structure 237 that interconnects the central guide post 232 and hollow pin guides 234. In this embodiment, the central guide post 232 is also hollow or cannulated so that the drill guide post 232 can slide over a guide rod 238 that extends through the femoral and tibial bone tunnels 132, 133.

In one embodiment, the soft tissue and skin 239 on each side of the incision are advantageously spread apart to keep them out of the way of the opening of the tibial tunnel 133 and so as to prevent them from interfering with the surgical procedure. The pin guides 234 may advantageously be used to keep the soft tissue and skin 239 in a desired spread apart fashion, as shown in FIG. 10. Once a pair of guide pins 240 have been driven into the tibia 122 and the drill guide 230 removed, the guide pins (e.g., breakaway guide pins 240) will maintain the soft tissue and skin 239 in the desired spread-apart orientation (FIG. 12).

With the drill guide 230 properly positioned, the guide pins can be driven into the tibia 122 using the pin guides 234 as a template. It will be appreciated that other templates for positioning the guide pins may be used. In the embodiment illustrated in FIGS. 11A–11C, a drill 242 is used to insert a pair of breakaway guide pins 240 into the tibia 122. The guide pins 240 may include appropriate tips (not shown) that facilitate drilling through bone. To facilitate breaking off excess length of the guide pins 240, each pin 240 may include breakaway notches or grooves 244, as illustrated in FIG. 12.

Figure 11A:
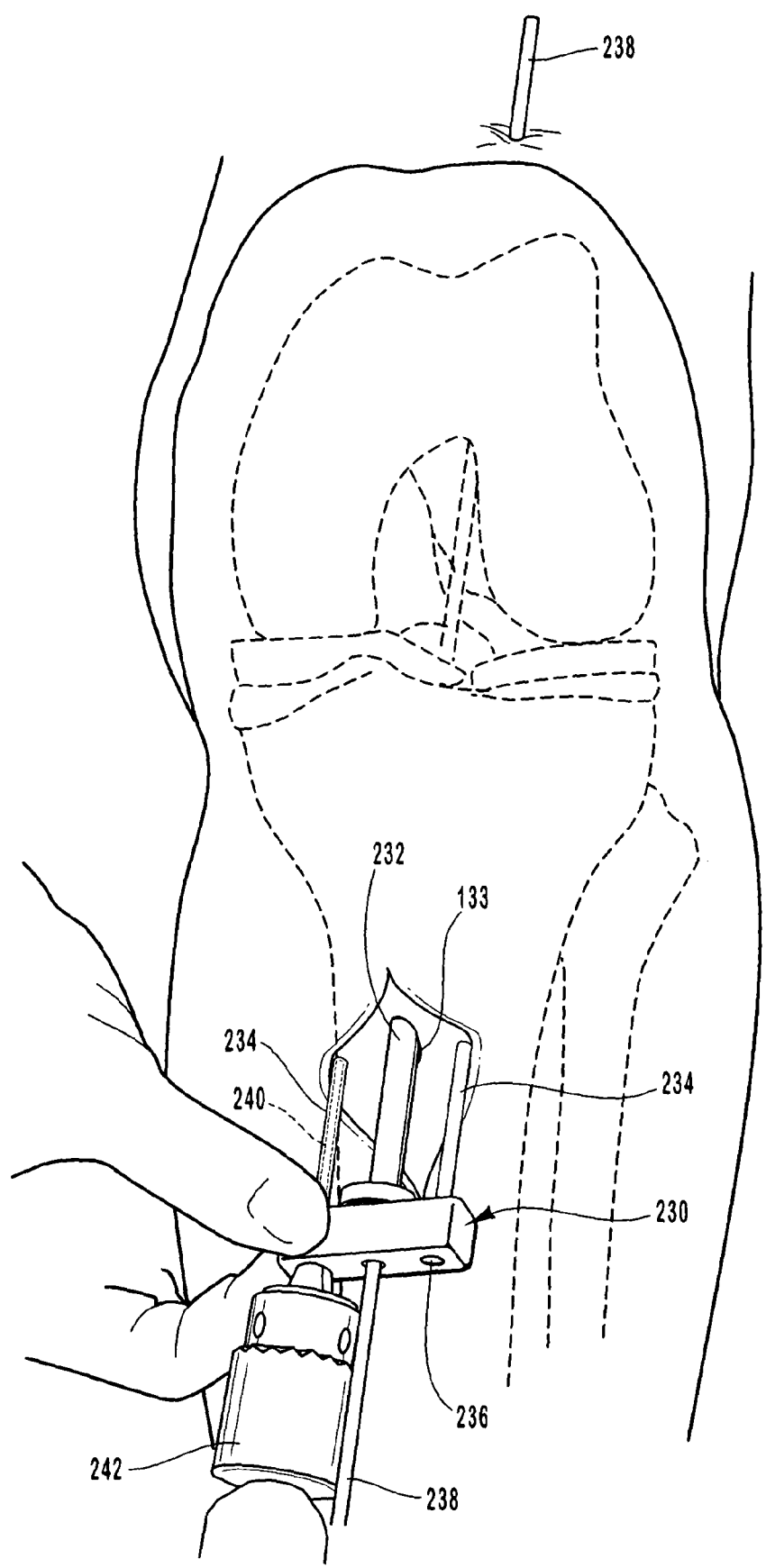
FIGS. 11A–11C illustrate an exemplary process in which a pair of guide pins are inserted into a patient's bone using a power drill and then portions broken off to yield implanted guide pins having an appropriate length.
Figure 11B:
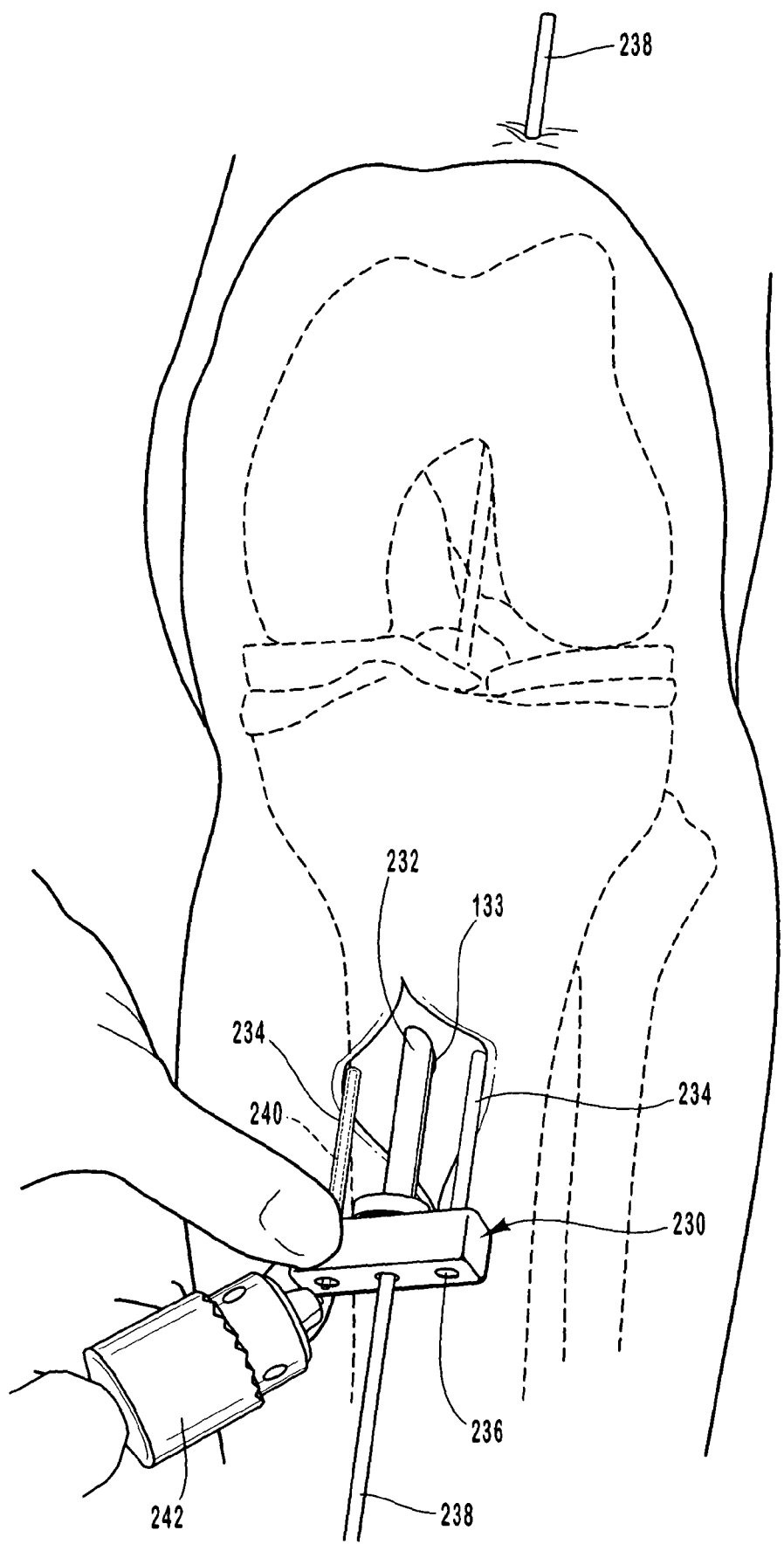
Figure 11C:
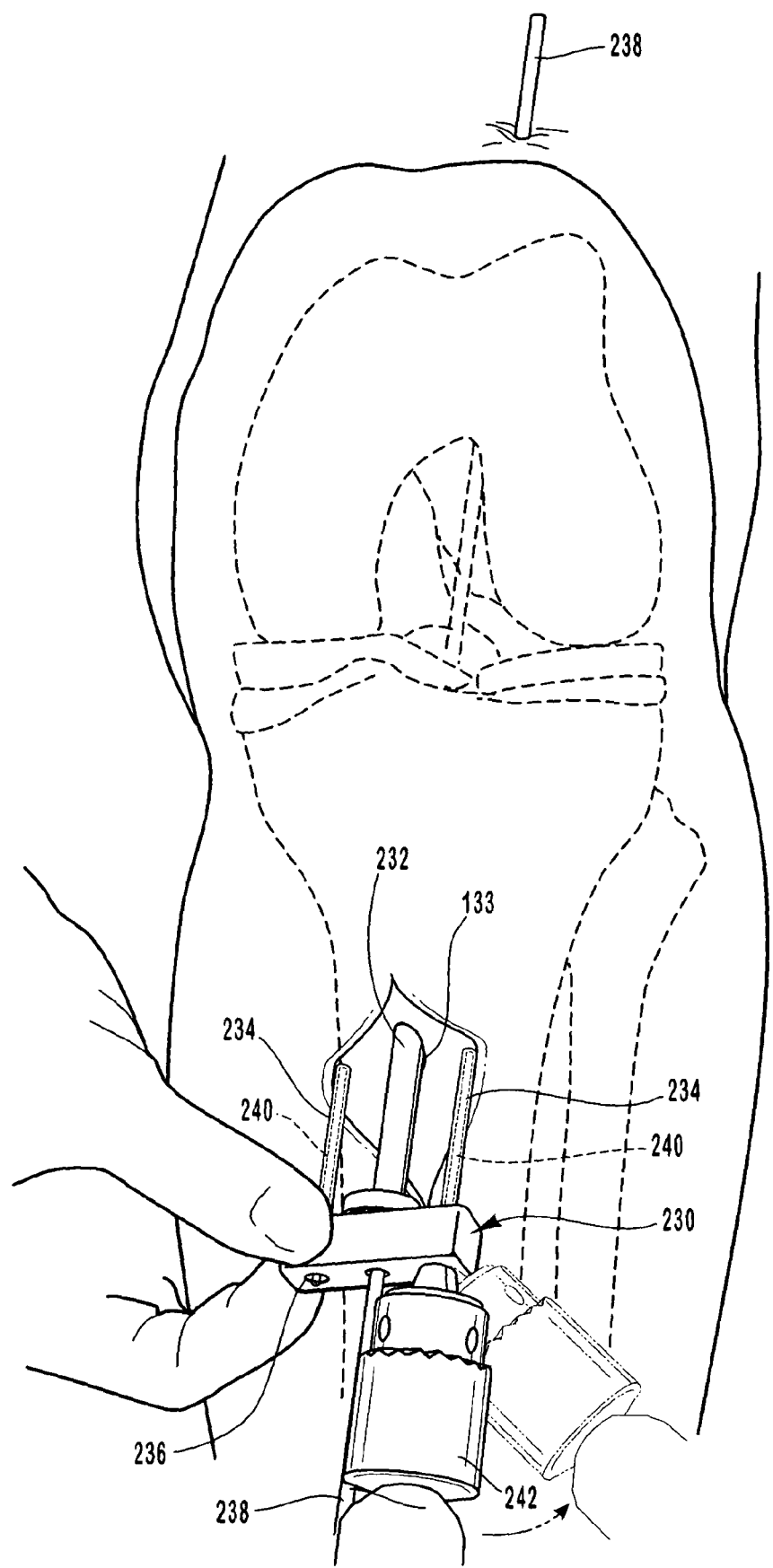

As shown in FIG. 11A, using the drill 242, a first guide pin 240 is drilled into the tibia 122 until a hard stop 246 (FIG. 12) on the pin 240 contacts bone (i.e., the hard cortical bone on the surface of the tibia 122). As shown in FIG. 11B, the breakaway guide pin 240 is broken off at the notch 244 nearest the drill guide aperture 236 by gripping the pin 240 near the aperture 236 and bending it until it breaks. This can be done, for example, using the drill 242. This process is repeated for the second guide pin (FIG. 11C).

Figure 12:
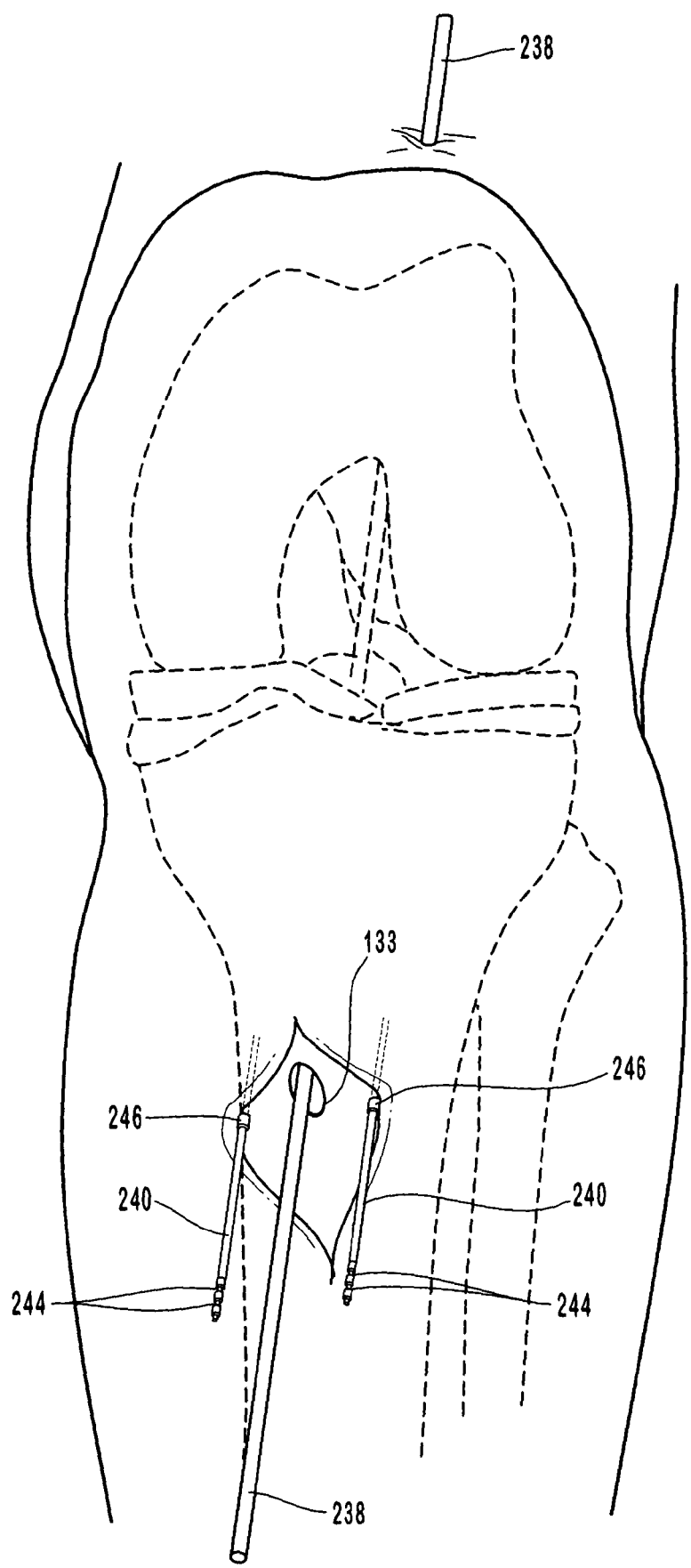
FIG. 12 shows a pair of guide pins implanted in a patient's bone near a bone tunnel into which a tissue graft is to be inserted and implanted.

The drill guide 230 is then removed, leaving behind the two guide pins 240 anchored within the tibia 122, as shown in FIG. 12. In addition to providing the structure upon which a tensioning device may be removably attached to the patient's tibia 122, the guide pins 240 also advantageously keep the soft tissue and skin 239 in the desired spread-apart orientation in order to maintain clear access to the tibial bone tunnel 133.

The composite soft tissue graft 226 is then drawn through the bone tunnels 133, 132 and secured to the femur using known surgical procedures. For example, the soft tissue graft 226 can be pulled cephalad through the tibial tunnel 133 and then the femoral tunnel 132 using graft passing sutures 212. The guide rod 238 may assist this process. For example, the guide rod 238 may include a suture eyelet (not shown), through which the graft passing sutures 212 can be pulled to draw the suture graft 226 through the bone tunnels 133, 132. When the forward end of the graft 236 has been properly placed in a desired location within the femoral tunnel 132, more particularly the doubled over ends of the loop graft bundles, the graft affixed in the femur using an interference screw or other fixation means known in the art. The two free ends of each graft bundle are initially unaffixed so as to facilitate conditioning and pre-tensioning of each graft bundle individually.

Figure 13:
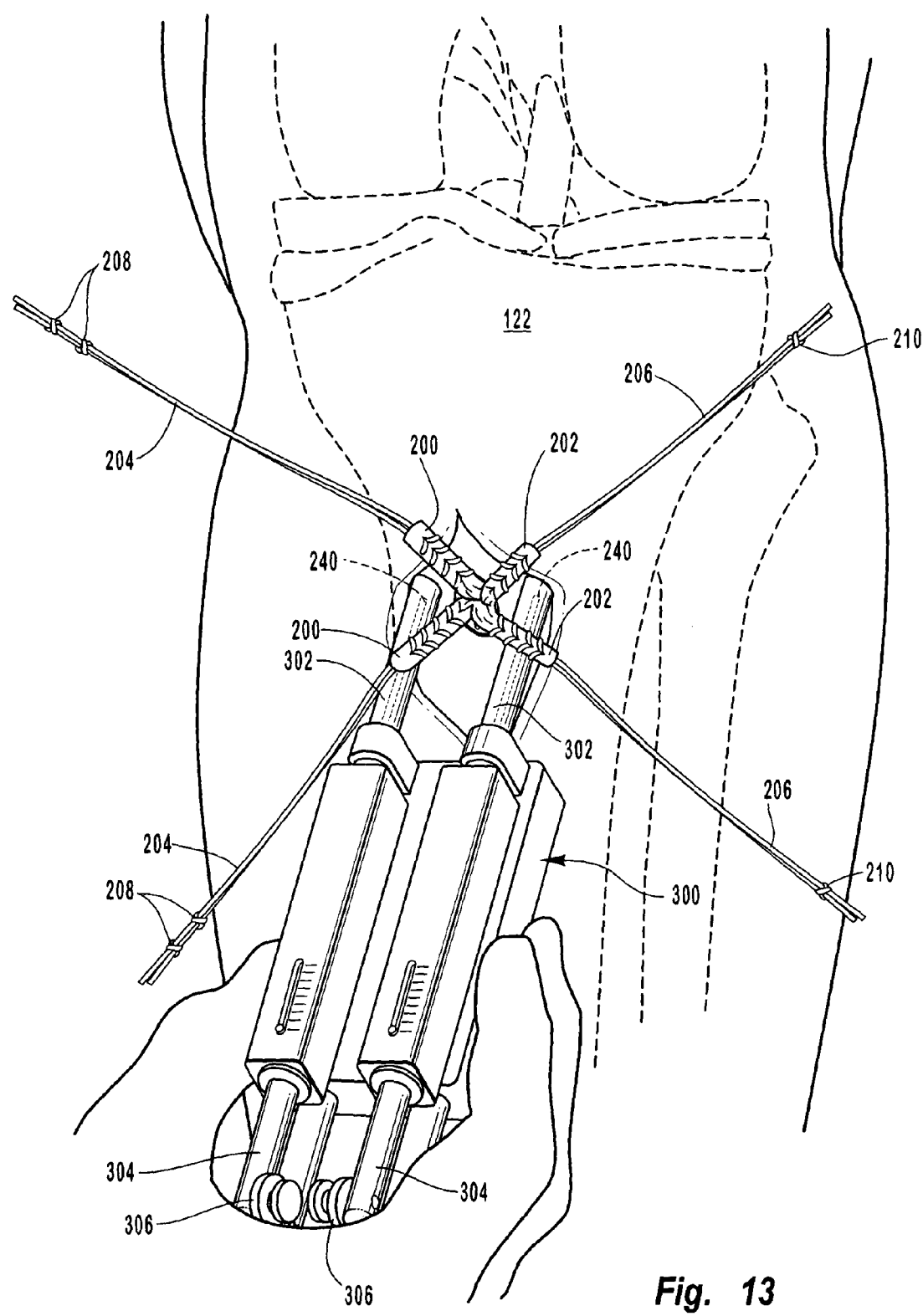
FIG. 13 illustrates a joint into which a multiple strand soft tissue graft has been inserted and then anchored at one end, together with a tensioning device according to the invention being positioned over guide pins preparatory to tensioning free ends of the tissue graft.

As shown in FIG. 13, the free ends of the semitendinosus tendon 200 and gracillis tendon 202 extend out from the tibial bone tunnel 133, together with their associated suture strands 204, 206. The graft 226 is now ready to be conditioned and pre-tensioned. The knots 208, 210 help identify to which of the grafts 200 or 202 the respective suture strands 204, 206 are attached. FIG. 13 also shows a tensioning device 300 being positioned on the tibia 122 adjacent to the tibial bone tunnel 133. The tensioning device 300 includes a pair of hollow attachment posts 302 that are slidably inserted over the guide pins 240 extending from the tibia 122. In this way the tensioning device 306 is slidably connected to the guide pins 240. It will appreciated that the attachment posts 302 may optionally include locking features that clamp or otherwise lock the tensioning device 300 to the guide pins 240 (e.g., features that mechanically engage the notches 244 of the guide pins 242. The tensioning device 300 also includes a pair of tensioning pistons 304 to which corresponding suture attachment pulleys 306 are rotatably attached.

The tensioning device 300 is similar to the tensioning device 10 described above in FIGS. 1–3 except that tensioning device 300 is not modular. Instead of having separate limb attachment and graft tensioning systems, the tensioning device 300 includes an integral limb attachment system comprising the aforementioned attachment posts 302. The separate drill guide 230 used to attach the guide pins 240 to the tibia 122 is removed and forms no part of tensioning device 300. In most other respects the tensioning device 300 functions similarly to tensioning device 10 to individually tension different graft strands or graft bundles of a soft tissue graft.

The next step involves attaching each of suture strands 204, 206 to a respective suture attachment pulley 306 of the tensioning device 300. This can be performed using any known tying or joining technique known in the art so as to result in the semitendinosus suture strand 204 being looped around one suture attachment pulley 306 and the gracillis suture strand 206 being looped around the other suture attachment pulley 306. Looping the suture strands 204, 206 around the suture attachment pulleys 306 equalizes the load or tension applied to the free ends of a respective graft strand 200, 202. It is generally preferable to avoid crossing or mismatching the different suture strands 204, 206, which would result in equalizing tension between the free ends of different graft strands 200, 202. Knots 208, 210 can be used to distinguish between the different suture strands 204, 206.

Figure 14:
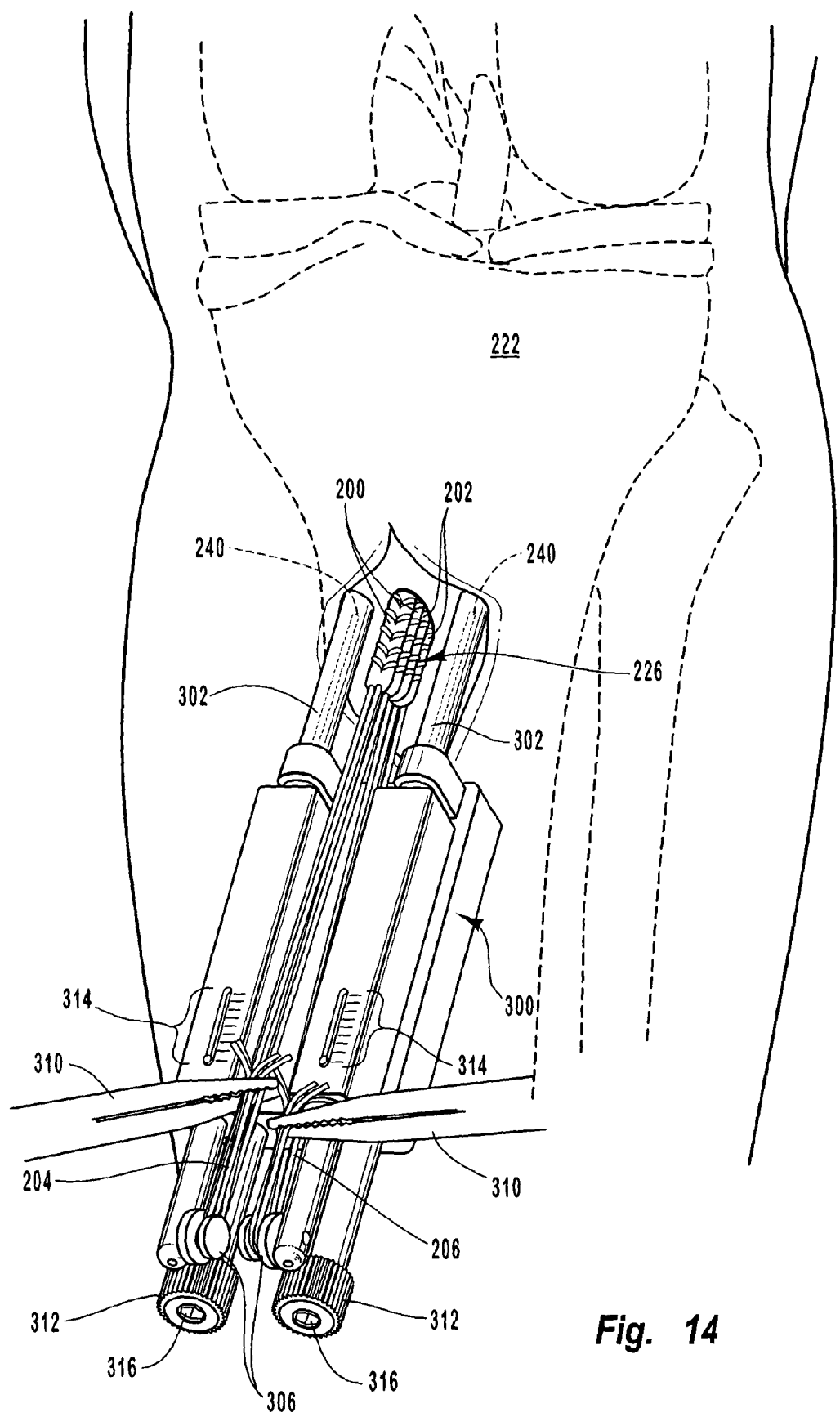
FIG. 14 shows a tensioning device according to the invention having a pair of suture attachment wheels to which a pair of corresponding looped sutures are attached.

FIG. 14 depicts an embodiment in which the suture strands 204, 206 are each clamped after being looped around a respective suture attachment pulley 306 by means of a respective suture clamp 310. If the suture clamps 310 are the only means of joining the free ends of the suture strands 204, 206 together, they may be left in place throughout the entire procedure until the free ends of the tissue graft strands 200, 202 have been secured to the tibia 122, more particularly within the tibial bone tunnel 133. The suture clamps 310 are advantageously attached in a manner or location that does not unduly obstruct or hinder proper use and functioning of the tensioning device 300. The tensioning device 300 is now ready to be used in conditioning and individually pre-tensioning the soft tissue graft strands 200, 202 of the composite graft 226.

Figure 15:
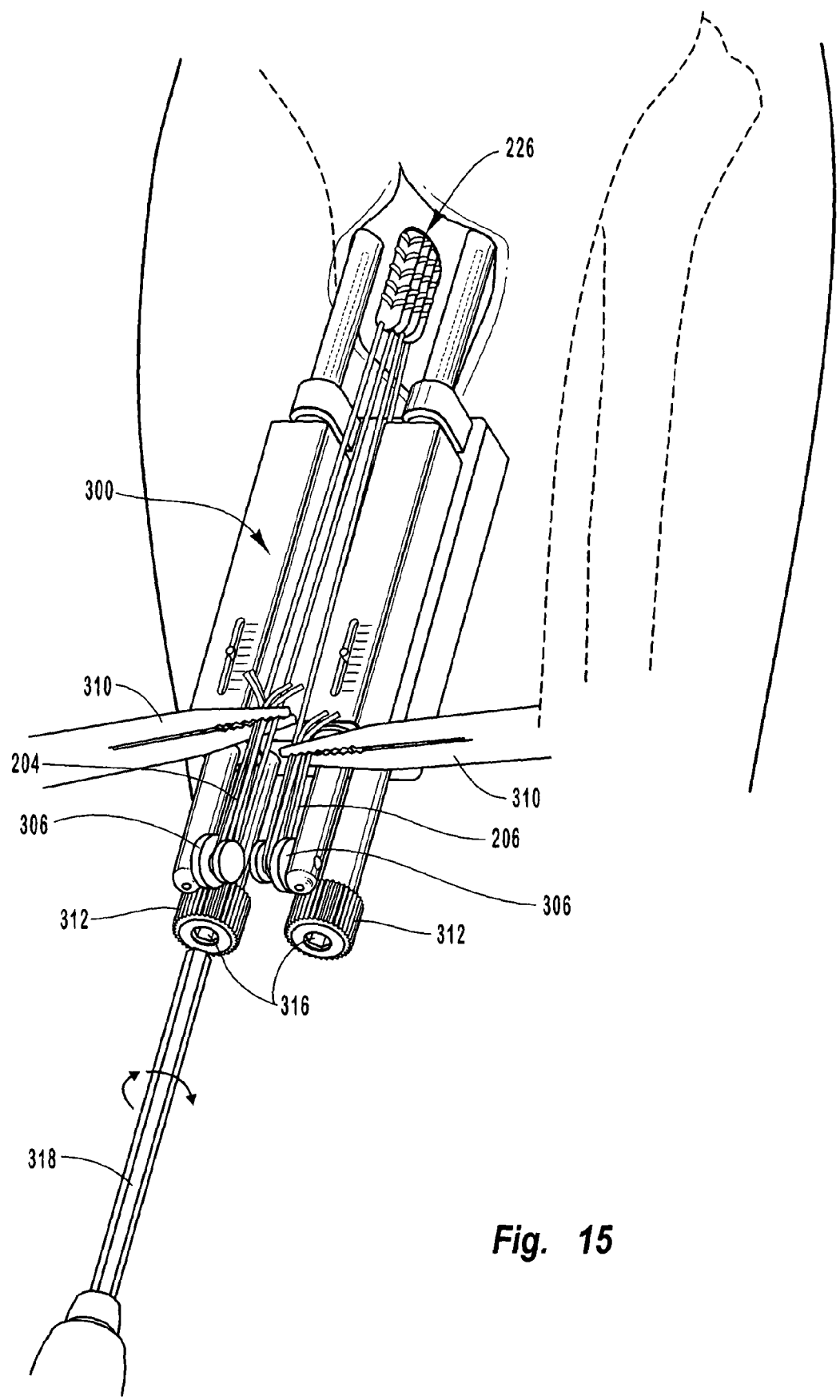
FIG. 15 shows the act of adjusting the tension applied to the free ends of a soft tissue graft bundle by rotating an adjustment knob.

As shown in FIGS. 14 and 15, the tensioning device 300 includes a pair of tension adjustment knobs 312, which interact with corresponding tensioning pistons 304 attached to the suture attachment wheels 306. By rotating the tension adjustment knobs 312, an individualized tension or tensile stress can be separately applied to each of the semitendinosus strand 200 and gracillis strand 202. Rotating the tension adjustment knob 312 in one direction increases the applied tension or tensile load, while rotating the knob 312 in the opposite direction decreases the applied tension. The tension that is individually applied to each graft strand 200, 202 can be determined by viewing a tension gauge 314 associated with each tensioning piston 304. The tension adjustment knobs 312 may optionally include a hexagonal shaped recess 316 or other appropriate recess, protrusion, or other mechanical feature that permits attachment of a driver 318 (FIG. 15) to the tension adjustment knob 312. This assists the user in applying a desired level of tension.

The amount of tension that is applied to each tissue graft strand 200, 202, as well as the composite graft 226, can be determined using known methods. In general, the respective amount of tension borne by each graft strand 200, 202 is related to its relative diameter. According to one embodiment, the amount of tension that will be applied to each tissue graft strand can be determined using a graft tensioning calculator 320 depicted in FIG. 16. The graft tensioning calculator 320 includes two parts that are moveable relative to each other, a first part or column 322 showing different graft bundle diameter values and a second part or column 324 showing different tensile load values in both metric (Newtons) and English (pounds) units.

The graft tensioning calculator 320 may be used as follows. First, using known methods, an overall graft tension is determined for the composite graft. Factors that may be used in determining the proper overall graft tension include the size, shape and flexibility of the tissue graft strands and/or composite graft, the size of the patient (height and/or weight), the age and/or sex of the patient, the desired level of stiffness or flexibility of the repaired joint, and the type of activities to which the repaired joint will be subjected. Once the overall graft tension is determined, the fraction or portion of the overall tension borne by each graft strand is then apportioned using the graft tensioning calculator 320.

Figure 16:
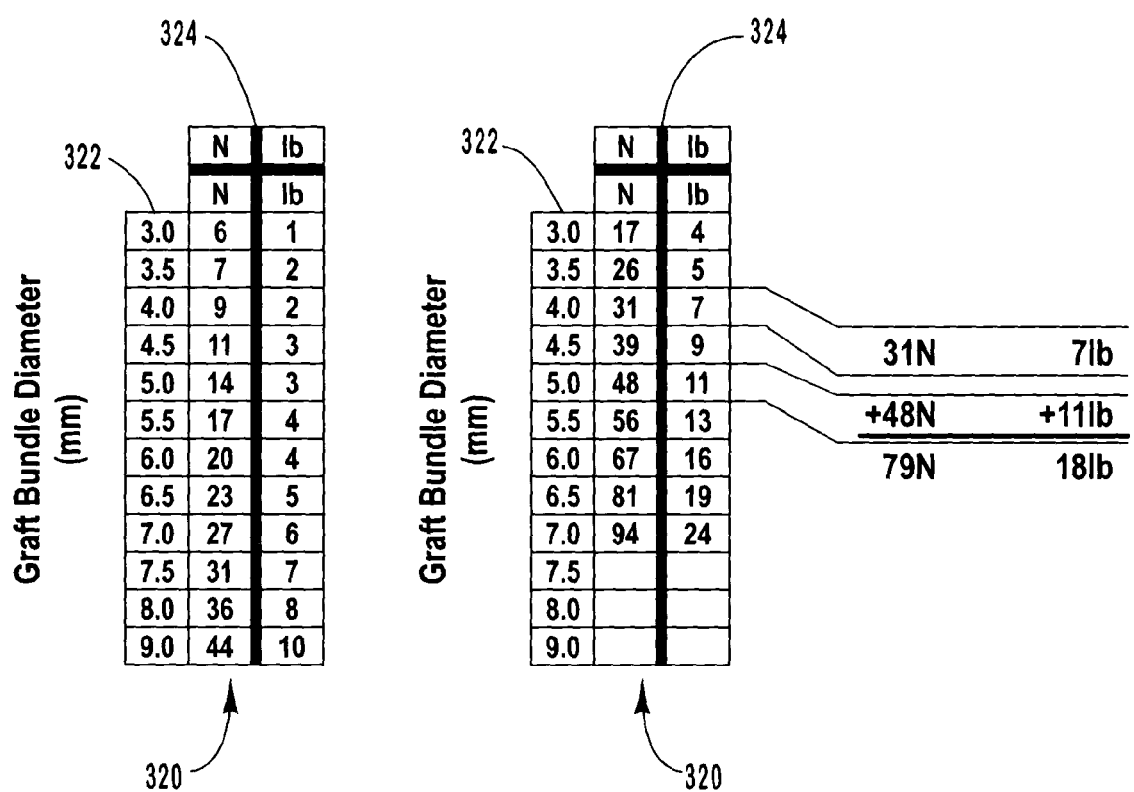
FIG. 16 illustrates a graft tension calculator used in determining the proper amount of tension or stress to be born by each strand of a two-stranded soft tissue graft based on the relative diameters of each doubled over strand or graft bundle.

FIG. 16 illustrates an example in which the looped or doubled over graft strands (or "graft bundles") have diameters of 4.0 and 5.0, respectively, and the desired overall graft tension is 79 N (18 lb). When the graft tensioning calculator 320 is in the initial configuration shown on the left, the corresponding tensile stress values for graft bundle diameters of 4.0 and 5.0 are 9 N (2 lb) and 14 N (3 lb), respectively. Adding these two tensile load values together does not yield the desired overall graft tension of 79 N (18 lb) but only 23 N (5 lb). Therefore, the graft tensioning calculator 320 is advantageously adjusted to yield the correct tensile loads to be applied to the graft bundles. In particular, the second column 324 containing the tensile load values is moved or reconfigured relative to the first column 322 containing the graft bundle diameters until the tensile load values corresponding to graft bundle diameters of 4.0 and 5.0 equal (or most closely approximate) 79 N (18 lb), as shown in the adjusted configuration on the right in FIG. 16. As shown, the tensile load values corresponding to 4.0 and 5.0 mm (31 N (7 lb) and 48 N (11 lb), respectively) add up exactly to 79 N (18 lb). It will be appreciated, however, that if the tensile load values do not add up exactly to the overall graft tension desired, the proper tensile load values can be approximated using known mathematical procedures. It is also appreciated that the use of graft tensioning calculator 320 having sliding columns 322 and 324 is merely illustrative. Other ways of determining the proper tensile load to be applied to each graft strand or graft bundle can be used (e.g., ratios that are determined using a variety of calculating systems, whether primarily electronic or mechanical).

Once the individual tensile loads to be applied to each graft bundle corresponding to the semitendinosus tendon graft 200 and gracillis tendon graft 202 have been determined, the tensioning device 300 is then used to apply an appropriate tensile load to each graft bundle. This may be performed, for example, by turning each tension adjustment knob 312 until its corresponding tension gauges 314 registers a desired tensile load value (FIG. 15). In one embodiment, tension is initially applied when the knee joint is oriented so that the femoral and tibial tunnels 132, 133 are aligned, which occurs at an angle of flexion of approximately 30°. In order to "condition" the semitendinosus tendon graft 200 and gracillis tendon graft 202 according to one embodiment, a "conditioning force" greater than the final tension is initially applied. The conditioning force is advantageously greater than the final tension to remove any slack in the system and compensate for stretching of the graft strands 200, 202 and/or tighter seating of the suture strands 204, 206. This helps prevent or minimize further stretching of the completed graft once secured to the tibia 122 at the final tension.

Once a proper conditioning force has been applied, the graft is ready to be conditioned. FIG. 17 shows the knee joint being cycled between full extension and deep flexion. This process is advantageously repeated until the applied tension reaches a stable mean value. The tension gauges 314 may be used to observe the excursion of each graft bundle during cycling as a measure of graft laxity. It may be necessary or desirable during the conditioning step to increase or decrease the tensile load applied to one or more of the graft bundles depending on observed changes in graft tension measured by the tension gauges 314. When the applied tension applied to each tissue graft bundle reaches a stable mean value, conditioning is complete and the final desired tensile force (e.g., determined using the graft tensioning calculator 320) is applied to each graft bundle. The conditioned and pre-tensioned composite tissue graft 226 is now ready to be secured to the tibia 122, more particularly, within the tibial bone tunnel 133.

Figure 19:
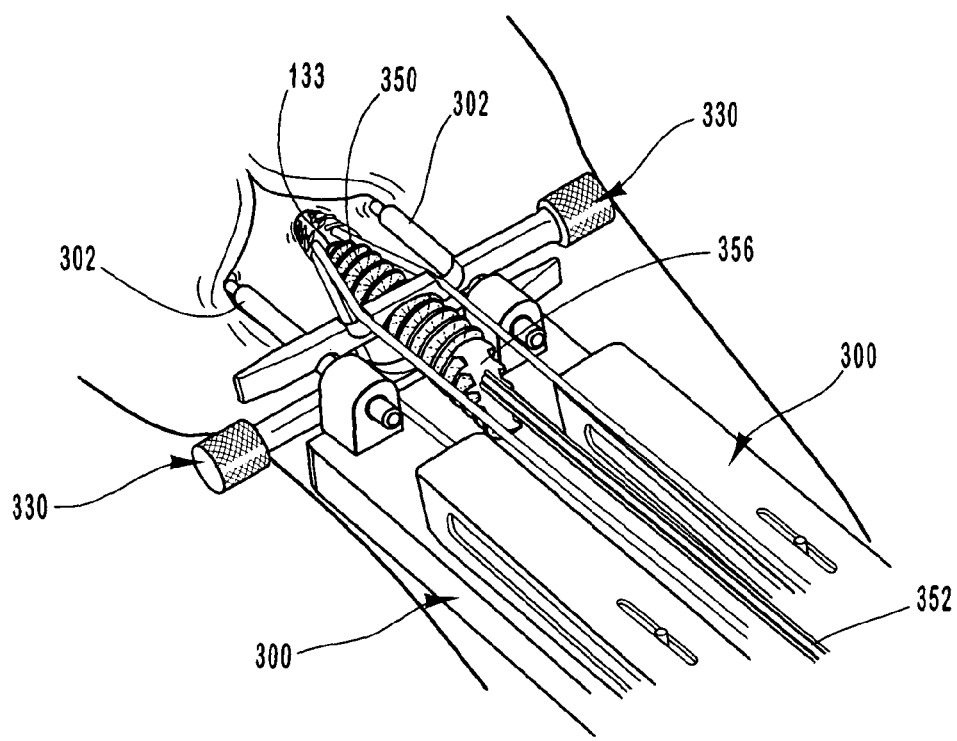
FIG. 19 illustrates the act of inserting an interference screw into a bone tunnel in order to secure the strands of a multi-stranded soft tissue graft against the inner wall of the bone tunnel.

According to one embodiment, as illustrated in FIG. 18, the suture strands 204, 206 are separated into four quadrants by means of a pair of suture strand separators 330. This, in turn, provides more clear access to the tibial tunnel 133 for insertion of an interference screw (FIG. 19). It also results in more even distribution of the four free, but yet unsecured, ends of the tissue graft strands 200, 202 around the perimeter of the tibial bone tunnel 133. Distributing the ends of the tissue graft strands 200, 202 over more of the surface area and perimeter of the tibial bone tunnel 133 results in a more concentric placement of an interference screw. This, in turn, is believed to result in a stronger final repaired knee joint. It will be appreciated that using suture strand separators 330 is but one way to provide this outcome.

As shown more particularly in FIG. 18A, the suture strand separators 330 include a gripping head 332 that aids in placing each suture strand separator 330 in a desired position relative to the tensioning device 300, more particularly, over and under the attachment posts 302 in a desired orientation and relative to the various suture strands 204, 206. A chiseled end 333 may be provided that aids in inserting the suture strand separators 330 between groups of suture strands. The suture strand separators 330 further include a first suture retention recess 334 nearer the gripper head 332 into which one quadrant of suture strands is placed and a second suture retention recess 336 nearer the chiseled end 333 into which anther quadrant of suture strands is placed. On the side of the suture strand separators 330 opposite first and second suture retention recesses 334, 336 are a pair of guide recesses 338 that correspond to, and receive at least partially therein, the attachment posts 302 when in use. Between the guide recesses 338 is a central recess 340 through which an interference screw and driver can be inserted to affix the tissue graft to the tibia 122 when the suture strand separators 330 are properly positioned.

In one embodiment, one suture strand separator 330 is placed on top of the attachment posts 302 in order to separate some of the suture strands into two upper quadrants, and a second suture strand separator 330 is placed under the attachment posts 302 in order to separate other of the suture strands into two lower quadrants. The mechanical engagement between the guide recesses 338 and attachment posts 302, in combination with an opposing force applied by the tensioned suture strands positioned within the suture retention recesses 334, 336, help lock the suture strand separators 330 in their desired positions relative to the attachment posts 302.

Figure 20:
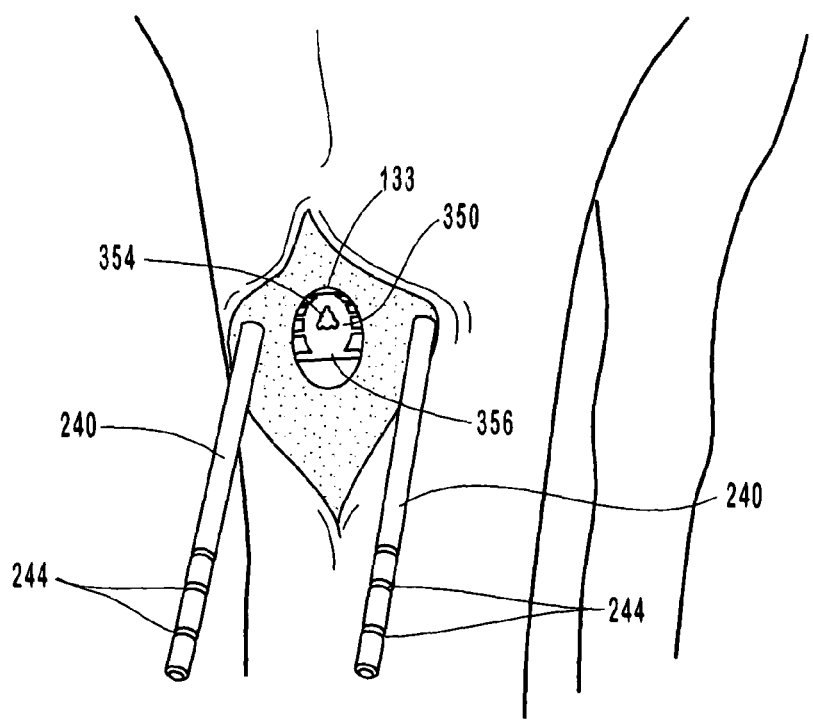
FIG. 20 shows the result of a soft tissue graft procedure after placement of an interference screw and removing any excess sutures and soft tissue graft ends.

After the suture strand separators 330 have been properly positioned so as to distribute the suture strands into four quadrants, the conditioned and pre-tensioned tissue graft 226 is ready to be secured to the tibia 122 using any securing or anchoring means known in the art. As illustrated in FIGS. 19 and 20, an interference screw 350 may be used. As shown in FIG. 19, an interference screw 350 attached to an appropriate driver 352 is inserted through the central recess 340 of the suture strand separators 330 and screwed into the tibial bone tunnel 133. The interference screw 350 advantageously includes a recess 354 (FIG. 20) that is designed to receive therein a correspondingly-shaped driving end of the driver 352. In one embodiment, the interference screw 350 may include an angled face 356 that is designed so as to lie substantially flush with the tibia 122 when screwed into the tibial tunnel 133. This obviates the need to cut or remove part of the interference screw 350. It is, of course, within the scope of the invention to remove (e.g., by cutting) any excess portion of the interference screw 350 that extends beyond the tibia 122.

Once the interference screw 350 or other securing means has been used to secure the tissue graft 226 to the tibia 122, the tensioning device 300 may be removed. In one embodiment, the suture clamps 310 are removed, which removes the tension applied to the sutures. This permits easy removal of the suture strand separators 330 from the tensioning device 300, and the tensioning device 300 from the tibia 122, leaving only the guide pins 240 (FIG. 20) and any excess tissue graft 226 and attached sutures 204, 206 emerging from the tibia 122. Any excess tissue graft 226 together with the attached sutures 204, 206 are easily removed by, e.g., cutting, such as by means of a scalpel, either before of after removal of the tensioning device 300 from the tibia 122.

The guide pins 240 are then removed and properly disposed of. Any remaining notches 244 may be used to assist in gripping the guide pins. In one embodiment, a drill (not shown) is used to unscrew the guide pins 240 from the tibia 122. After removing the guide pins 240, the soft tissue and skin 239 are brought back together and stitched, stapled, or otherwise reconnected to close the incision. Suitable post-operation recovery techniques may be employed to ensure proper healing.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A tensioning system for use in joint repair surgery involving independent tensioning of multiple tissue graft strands attached to a bone tunnel, the tensioning system comprising:
    a plurality of breakaway guide pins adapted for attachment to a patient's bone, each breakaway guide pin including one or more notches or grooves that facilitate preferential breakage of the guide pin at or near the one or more notches or grooves, the one or more notches or grooves being spaced apart from a tip of the guide pin so that, after insertion of the guide pin into a patient's bone and breaking off a first portion of the guide pin, a remaining portion of the guide pin will extend from a patient's leg; and
    a tensioning device that provides for independent tensioning of multiple tissue graft strands attached to a bone tunnel, the tensioning device comprising:
        an attachment portion comprising a plurality of attachment posts, each configured to slidably attach to one of said breakaway guide pins when positioned in a bone so as to extend from a patient's leg; and
        a tensioning portion configured to independently apply a desired tensile load to each of at least two separate strands of a soft tissue graft, the tensioning portion comprising:
            a tensioning block;
            a first adjustable tensioning apparatus attached to the tensioning block and configured so as to selectively increase or decrease a first tensile load applied to a first strand of a soft tissue graft in communication with the first adjustable tensioning apparatus; and
            a second adjustable tensioning apparatus attached to the tensioning block in a spaced-apart relationship wit the first adjustable tensioning apparatus and configured so as selectively increase or decrease a second tensile load applied to a second strand of the soft tissue graft in communication wit the second adjustable tensioning apparatus independently of the first tensile load applied by the first adjustable tensioning apparatus,
            the tensioning block maintaining a sufficient space between the first and second adjustable tensioning apparatus as to permit an interference screw to pass between the first and second adjustable tensioning apparatus while securing a soft tissue graft to the bone tunnel.

2. A tensioning system as defined in claim 1, wherein the breakaway guide pins are designed to be used only once and then discarded.

3. A tensioning system as defined in claim 1, each attachment post further comprising a hollow portion adapted to slidably receive therein one of the guide pins.

4. A tensioning system as defined in claim 1, each of the first and second adjustable tensioning apparatus comprising:
    a tensioning piston adapted to receive and secure thereto one or more sutures attached to at least one soft tissue graft strand;
    a hollow cylinder slidably disposed around at least a portion of the tensioning piston; and
    a spring disposed within the hollow cylinder and communicating between the hollow cylinder and tensioning piston so as to increase the tensile load applied by the tensioning piston onto the soft tissue graft strand as the spring is compressed.

5. A tensioning system as defined in claim 4, the tensioning piston further comprising a suture attachment wheel rotatably attached thereto.

6. A tensioning system as defined in claim 4, further comprising a tensioning bolt in threadable communication with the hollow cylinder so that selective rotation of the tensioning bolt causes corresponding movement of the hollow cylinder relative to the tensioning bolt.

7. A tensioning system as defined in claim 1, further comprising one or more tensile load gauges that display the tensile load applied by each of the first and second tensioning apparatus.

8. A tensioning system as defined in claim 1, wherein the attachment portion and the tensioning portion are nonremovably joined together.

9. A tensioning system as defined in claim 1, further comprising at least one suture strand separator configured for removable attachment to the tensioning device and adapted to maintain at least two suture strands attached to different ends of a multi-strand tissue graft in a desired space-apart relationship.

10. A tensioning system as defined in claim 1, further comprising a tension calculator adapted for determining what portion of a total tensile load to be applied to a composite tissue graft is to be applied to each tissue graft strand individually.

11. A tensioning system for use in joint repair surgery involving independent tensioning of multiple tissue graft strands attached to a bone tunnel, the tensioning system comprising:
    a tensioning device that provides for independent tensioning of multiple tissue graft strands attached to a bone tunnel, the tensioning device comprising:
        an attachment portion configured to removably attach the tensioning device to a person's limb; and
        a tensioning portion configured to independently apply a desired tensile load to each of at least two separate stands of a soft tissue graft, the tensioning portion comprising:
            a tensioning block;
            a first adjustable tensioning apparatus attached to the tensioning block and configured so as to selectively increase or decrease a first tensile load applied to a first strand of a soft tissue graft in communication with the first adjustable tensioning apparatus; and
            a second adjustable tensioning apparatus attached to the tensioning block in a spaced-apart relationship with the first adjustable tensioning appratus and configured so as selectively increase or decrease a second tensile load applied to a second strand of the soft tissue graft in communication with the second adjustable tensioning apparatus independently or the first tensile load applied by the first adjustable tensioning apparatus, the tensioning block maintaining a sufficient space between the first and second adjustable tensioning apparatus as to permit an interference screw to pass between the first and second adjustable tensioning apparatus while securing a soft tissue graft to the bone tunnel; and at least one suture strand separator configured for removable attachment to the tensioning device and adapted to maintain at least two suture strands attached to different ends of a multi-strand tissue graft in a desired space-apart relationship.

12. A tensioning system as defined in claim 11, the suture strand separator comprising a gripping head and a chiseled end opposite the gripping head that facilitates insertion of the suture strand separator between two or more suture strands.

13. A tensioning system as defined in claim 11, the suture strand separator comprising a first retention recess adapted to receive a first suture strand or group of suture strands and a second retention recess adapted to receive a second suture strand or group of suture strands, the first and second retention recesses being spaced-apart so as to maintain the first mid second suture strands or groups of suture strands in the desired spaced-apart relationship.

14. A tensioning system as defined in claim 13, the suture strand separator comprising a pair of spaced-apart guide recesses adapted to mate with a pair of corresponding attachment posts within the attachment portion of the tensioning device.

15. A tensioning system as defined in claim 14, the tensioning system comprising two suture strand separators that are adapted to separate four suture strands or groups of suture strands into four spaced-apart quadrants.

16. A tensioning system as defined in claim 15, the two suture strand separators, when placed together to form a composite device so that the first and second retention recesses of one suture strand separator are on one side of the composite device and the first and second retention recesses of the other suture strand separator are on opposite side of the composite device, defining a central recess approximately midway between the sides of the composite device through which an interference screw can be inserted to affix a soft tissue graft to a bone tunnel when the tensioning system is in use.

17. A tensioning system as defined in claim 11, further comprising a tension calculator adapted for determining what portion of a total tensile load to be applied to a composite tissue graft is to be applied to each tissue graft strand individually.

18. A tensioning system for use in joint repair surgery involving independent tensioning of multiple tissue graft strands attached to a bone tunnel, the tensioning system comprising:

a tensioning device that provides for independent tensioning of multiple tissue graft strands attached to a bone tunnel, the tensioning device comprising:

an attachment portion configured to removably attach the tensioning device to a person's limb; and a tensioning portion configured to independently apply a desired tensile load to each of at least two separate strands of a soft tissue graft, the tensioning portion comprising:

a first adjustable tensioning apparatus configured so as to selectively increase or decrease a first tensile load applied to a first strand of a soft tissue graft in communication with the first adjustable tensioning apparatus; and a second adjustable tensioning apparatus configured so as selectively increase or decrease a second tensile load applied to a second strand of the soft tissue graft in communication with the second adjustable tensioning apparatus independently of the first tensile load applied by the first adjustable tensioning apparatus; and a tension calculator adapted for determining what portion of a total tensile load to be applied to a composite tissue graft is to be applied to each tissue graft strand individually.

19. A tensioning system as defined in claim 18, further comprising a plurality of breakaway guide pins adapted for attachment to a patient's bone, each breakaway guide pin including one or more notches or grooves that facilitate preferential breakage of the guide pin at or near the one or more notches or grooves.

20. A tensioning system as defined in claim 19, the one or more notches or grooves of each breakaway guide pin being spaced apart from a tip of the guide pin so that, after insertion of the guide pin into a patient's bone and breaking off a first portion of the guide pin, a remaining portion of the guide pin will extend from a patient's leg.

21. A tensioning system as defined in claim 18, further comprising at least one suture stand separator configured for removable attachment to the tensioning device and adapted to maintain at least two suture strands attached to different ends of a multi-strand tissue graft in a desired space-apart relationship.

22. A tensioning system as defined in claim 18, each of the first and second adjustable tensioning apparatus further comprising a suture attachment wheel rotatably attached thereto.

23. A tensioning system for use in joint repair surgery involving independent tensioning of multiple tissue graft strands attached to a bone tunnel, the tensioning system comprising:

a plurality of breakaway guide pins adapted for attachment to a patient's bone, each breakaway guide pin including one or more notches or grooves that facilitate preferential breakage of the guide pin at or near the one or more notches or grooves and a protrusion positioned between a tip and the one or more notches or grooves that limits how far the guide pin can be inserted into a bone; and a tensioning device that provides for independent tensioning of multiple tissue graft strands attached to a bone tunnel, the tensioning device comprising:

an attachment portion comprising a plurality of attachment posts, each configured to slidably attach to one of said breakaway guide pins when positioned in a bone so as to extend from a patient's leg; and a tensioning portion configured to independently apply a desired tensile load to each of at least two separate strands of a soft tissue graft, the tensioning portion comprising:

a tensioning block;

a first adjustable tensioning apparatus attached to the tensioning block and configured so as to selectively increase or decrease a first tensile load applied to a first strand of a soft tissue graft in communication with the first adjustable tensioning apparatus;

a second adjustable tensioning apparatus attached to the tensioning block in a spaced-apart relationship with the first adjustable tensioning appratus and configured so as selectively increase or decrease a second tensile load applied to a second strand of the soft tissue graft in communication with the second adjustable tensioning apparatus independently of the first tensile load applied by the first adjustable tensioning apparatus; and the tensioning block maintaining a sufficient space between the first and second adjustable tensioning apparatus as to permit an interference screw to pass between the first and second adjustable tensioning apparatus while securing a soft tissue graft to the bone tunnel.

24. A tensioning system as defined in claim 23, further comprising a tension calculator adapted for determining what portion of a total tensile load to be applied to a composite tissue graft is to be applied to each tissue graft strand individually.

* * * * *

UNITED STATES PATENT AND TRADEMARK OFFICE
CERTIFICATE OF CORRECTION

| | |
|---|---|
| PATENT NO. | : 7,118,578 B2 |
| APPLICATION NO. | : 10/651671 |
| DATED | : October 10, 2006 |
| INVENTOR(S) | : West, Jr. et al. |

It is certified that error appears in the above-identified patent and that said Letters Patent is hereby corrected as shown below:

Column 14
Line 29, change "conditioning" to --condition--
Line 30, change "pre-tensioning" to --pre-tension--

Column 18
Line 42, change "100" to --166--

Column 21
Line 25, change "306" to --300--

Column 25
Line 58, change "wit" to --with--

UNITED STATES PATENT AND TRADEMARK OFFICE
CERTIFICATE OF CORRECTION

PATENT NO. : 7,118,578 B2
APPLICATION NO. : 10/651671
DATED : October 10, 2006
INVENTOR(S) : West, Jr. et al.

It is certified that error appears in the above-identified patent and that said Letters Patent is hereby corrected as shown below:

Drawings
Sheet 19, replace Fig. 10 with the figure depicted herein below, wherein the central guide post has been labeled with --232--

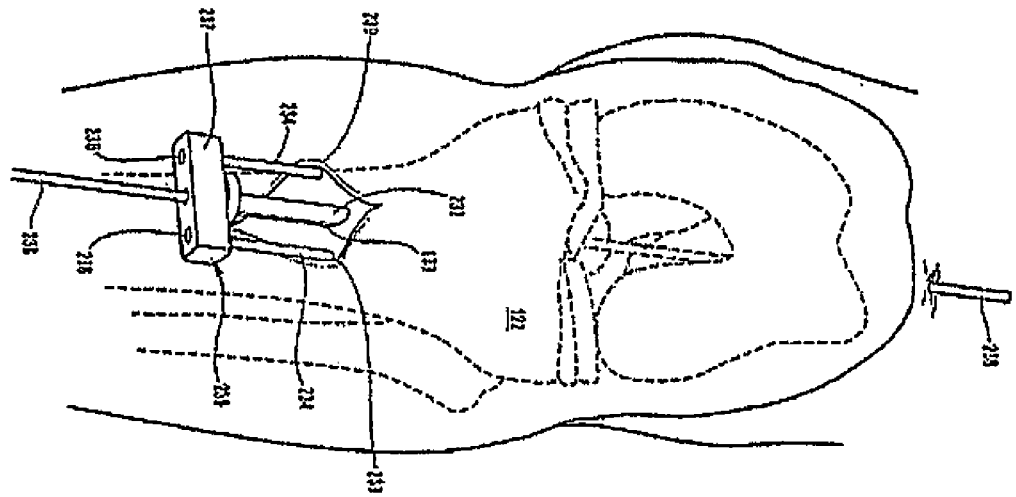

Signed and Sealed this

Thirtieth Day of October, 2007

JON W. DUDAS
*Director of the United States Patent and Trademark Office*